US006759227B2

(12) United States Patent
van de Craen et al.

(10) Patent No.: US 6,759,227 B2
(45) Date of Patent: Jul. 6, 2004

(54) CASPASE HOMOLOGUE

(75) Inventors: Marc van de Craen, Ghent (BE); Wim Declercq, Marke (BE); Peter Vandenabeele, Sint-Amandsberg (BE); Walter Fiers, Destelbergen (BE)

(73) Assignee: Vlaams Interuniversitair Instituut Voor Biotechnologie VZW, Zwijnaarde (BE)

( * ) Notice: Subject to any disclaimer, the term of this patent is extended or adjusted under 35 U.S.C. 154(b) by 139 days.

(21) Appl. No.: 09/764,803

(22) Filed: Jan. 17, 2001

(65) Prior Publication Data

US 2002/0034812 A1 Mar. 21, 2002

Related U.S. Application Data

(63) Continuation of application No. PCT/EP99/04939, filed on Jul. 12, 1999.

(30) Foreign Application Priority Data

Jul. 17, 1998 (EP) .............................................. 98202422

(51) Int. Cl.$^7$ ................................................. C12N 9/50
(52) U.S. Cl. ...................... 435/219; 435/183; 435/212; 435/219; 435/424; 435/94.1; 435/94.63
(58) Field of Search ................................ 435/183, 212, 435/219; 424/94.1, 94.63

(56) References Cited

U.S. PATENT DOCUMENTS

| 6,340,740 B1 | 1/2002 | Alnemri et al. |
| 6,376,226 B1 | 4/2002 | Alnemri |
| 6,432,628 B1 | 8/2002 | Alnemri et al. |
| 2002/0081705 A1 | 6/2002 | Mankovich |
| 2002/0146804 A1 | 10/2002 | Alnemri |

FOREIGN PATENT DOCUMENTS

| WO | WO 91/03551 | 3/1991 |
| WO | WO 96/20276 | 4/1996 |
| WO | WO 96/13603 | 5/1996 |
| WO | WO 99/10504 | 3/1999 |
| WO | WO 00/04169 | 1/2000 |

OTHER PUBLICATIONS

Poyet et al. Accession P31944. Jul. 1, 1993 (Alignment No. 1).*
Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
Abstract XP–002085023.
Abstract XP–002085024.
Abstract XP–002085055.
Abstract XP–002092996.
Fernandes–Alnemri et al., "CPP32, a Novel Human Apoptotic Protein with Homology to *Caenorhabditis elegans* Cell Death Protein Ced–3 and Mammalian Interleukin–1 β–converting Enzyme", *The Journal of Biological Chemistry*, vol. 269, No. 49, pp. 30761–30764, Dec. 9, 1994.
Hu et al., "Caspase–14 Is a Novel Developmentally Regulated Protease", *The Journal of Biological Chemistry*, vol. 273, No. 45, pp. 29648–29653, Nov. 6, 1998.
Juan et al., "Identification and Mapping of Casp7, a Cysteine Protease Resembling CPP32β, Interleukin–1β Converting Enzyme, and CED–3", *Genomics*, 40, pp. 86–93, 1997.
PCT International Preliminary Examination Report, PCT/EP99/04939, dated Sep. 19, 2000.
PCT International Search Report, PCT/EP99/04939, dated Aug. 24, 1999, 7 pages.
Van de Craen et al., "Identification of a new caspase homologue: caspase–14", *Cell Death and Differentiation*, 5, pp. 838–846, 1998.
Cohen, Caspases: the executioners of apoptosis, Biochem J., 1997, pp. 1–16, vol. 326.
Rendl et al., Caspase–14 Expression by Epidermal Keratinocytes is Regulated by Retinoids in a Differentiation–associated Manner, The Journal of Investigative Dermatology, 2002, pp. 1150–1155, vol. 119, No. 5.
Haake et al., Apoptosis: A Role in Skin Aging? J. Investig. Dermatol. Symp. Proc., Aug. 1998, pp. 28–35, vol. 3, No. 1.

* cited by examiner

*Primary Examiner*—Ponnathapu Achutamurthy
*Assistant Examiner*—Christian L. Fronda
(74) *Attorney, Agent, or Firm*—TraskBritt

(57) ABSTRACT

Caspases are cysteinyl aspartate-specific proteinases, many of which play a central role in apoptosis. This invention relates to the identification of a new murine caspase and its human homologue. The new molecules are most related to human/murine caspase-2 and human caspase-9 and possesses all the typical amino acid residues of the caspases involved in catalysis, including the QACRG box, and contains no or only a very short prodomain. Northern blot analysis revealed that mRNA expression of the new caspase is predominant in skin.

2 Claims, 12 Drawing Sheets

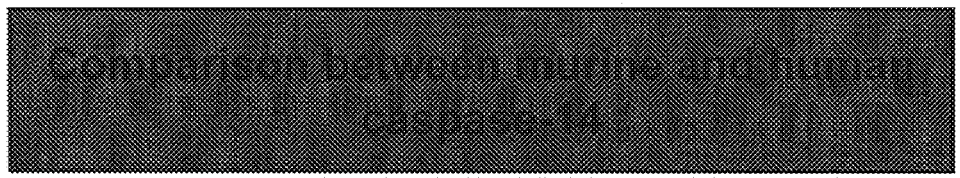

```
                  1         10      ▼20       30        40        50
                  |---------+---------+---------+---------+---------|
        murine    NESEKSDPQPLQEERYDNSGARLALTLCVTKAREGGEVDIEALERHFRYL
        human     MSNPRSLEEEKYDNSGARLALILCVTKAREGSEEDLQALEKHFRQL
        Consensus MS#PrpLBEErYDNSGARLALiLCVTkAREgSEeD$$ALErMFRqL 51        60        70        80    ✻  90       100
                  |---------+---------+---------+---------+---------|
        murine    RFESTNKRBPTAQAFLEELDEFQQTIDNWEEPVSCAFVVLNANGEEGILK
        human     RFESTNKRBPTAEQFQEELEKFQQRIDSREDPVSCAFVVLNBNGREGFLK
        Consensus rFESTNKRBPTA#QFqEEL#eFQQaIDnrE#PVSCAFVVLNANGrEGILK
                                                                ___

101       110       120       130       140       150
                  |---------+---------+---------+---------+---------|
        murine    GEDEKNVRLEDLFEVLNBKNCKRLSGKPKVYIIQICRGENRDPGEELRGN
        human     GEDGENVKLENLFEALNBKNCQRLRAKPKVYIIQRCKGEQRDPGEIV----
        Consensus GEDeeNVrLE#LFEaLNBKNCqRLRaKPKVYIIQRCRGEqRDPGEel
                                                   _____

151    ▼160 ▼      170       180   ✻   190       200
                  |---------+---------+---------+---------+---------|
        murine    EELGGDEELGGDEVAVLKNNPQSIPTYYDTLHIYSTVEGYLSYRNDEKGS
        human     ----GGDEI-----YNVIKDSPQTIPTYIDRLHVYSTVEGYIRYRHDQKGS
        Consensus     GGDEe     YaV#K#nPQsIPTYYDaLH!YSTVEGYiaYRH#KGS
                                                                   ✻✻

201       210       220       230       240      250
                  |---------+---------+---------+---------+---------|
        murine    GFIQTLTDVFINNKGSILELTEEITRLMANTEVHQEGKPRKVNPEVQSTL
        human     CFIQTLVDVFTKNKGHILELLTEVTRRMAERELVQEGKARKTNPEIQSTL
        Consensus cFIQTLtDVFihrKGhILELleE!TRrMA#aELnQEGKaRKt#PEIQSTL 251 257
                  |-----|
        murine    KKRLYLQ
        human     RKRLYLQ
        Consensus RKrLYLQ
```

CASPASE HOMOLOGUE

CROSS-REFERENCE TO RELATED APPLICATIONS

This application is a continuation under 35 U.S.C. §§ 120 and 365(c) of pending application PCT/EP99/04939 filed on Jul. 12, 1999 designating the United States of America, which itself claims priority from European Patent Application EP 98202422.6, filed on Jul. 17, 1998.

BACKGROUND OF THE INVENTION

1. Field of the Invention

Caspases are cysteinyl aspartate-specific proteinases, many of which play a central role in apoptosis. This invention relates to the identification of a new murine caspase and its human homologue. The new molecules are most related to human/murine caspase-2 and human caspase-9 and possesses all the typical amino acid residues of the caspases involved in catalysis, including the QACRG box, and contains none, or only a very short prodomain. Northern blot analysis revealed that mRNA expression of the new caspase is predominant in skin. The invention thus relates to a new caspase homologue and its use to treat human and/or animal diseases, especially skin or skin related diseases.

2. State of the Art

Members of the caspase protein family are key mediators in the execution of apoptotic cell death. Specific inhibition of one or more caspases by CrmA, p35 or the peptide derivatives Ac-YVAD-CHO and Ac-DEVD-CHO revealed that several caspases are involved in apoptosis, mediated by stimulated Fas or 55-kDa tumor necrosis factor receptor (Los et al, 1995; Bertin et al, 1997; Nagata, 1997). Both receptors transduce the death signal through a cytoplasmic sequence motif called "death domain" (DD). After receptor trimerization this domain rapidly associates with a similar DD in the adapter molecules TRADD and/or FADD. The N-terminal end of FADD exhibits significant sequence homology to two similar regions within the prodomain of procaspase-8 and procaspase-10, referred to as death effector domains (DED), which allow heterodimerization of these caspases with FADD (Boldin et al, 1996; Muzio et al, 1996; Vincenz and Dixit, 1997). In the case of Fas, it has been demonstrated that receptor occupation results in FADD-mediated recruitment of procaspase-8 into the receptor complex. Receptor-associated procaspase-8 is then proteolytically cleaved to generate active caspase-8 (Yang et al, 1998). Once procaspase-8 becomes activated, it might initiate a proteolytic caspase activation cascade, since it is able to process, at least in vitro, all known caspases into their active subunits (Srinivasula et al, 1996). Activated caspases are believed to be the executors of cell death by aspartate-specific proteolysis of substrates, which results in the characteristic features of apoptosis, such as DNA degradation, nuclear condensation, membrane blebbing, etc. (Villa et al, 1997).

SUMMARY OF THE INVENTION

A first aspect of the current invention concerns proteins and functional fragments thereof forming new members of the caspase family. Another aspect of the invention relates to nucleic acids encoding the new members of the caspase family. The invention also pertains to the screening for compounds that inhibit the synthesis and/or biological activity of the new members of the caspase family. Another aspect of the present invention is the use of these proteins, nucleic acids and/or compounds in diagnosis and/or treatment of human and/or animal diseases, especially skin diseases and/or inappropriate wound healing. A further aspect of the invention is the use of the proteins, nucleic acids or compounds to modulate keratinization. In addition a pharmaceutical preparation to treat human and/or animal diseases, especially skin diseases, comprising proteins, nucleic acids or compounds belong to the scope of the invention.

AIMS AND DESCRIPTION OF THE INVENTION

The invention thus concerns a caspase-like polypeptide comprising SEQ. ID. NO. 2 or a polypeptide with at least 80% homology to the sequence or a functional fragment of the polypeptides. In addition, the invention relates to a human caspase-like polypeptide comprising SEQ. ID. NO. 4 or a polypeptide with at least 80% homology to the sequence or a functional fragment of the polypeptides.

The invention also pertains to an isolated nucleic acid molecule comprising a nucleotide sequence encoding a polypeptide or a functional fragment thereof as mentioned above. Part of the invention is also an isolated nucleic acid molecule comprising SEQ. ID. NC). 1 or SEQ. ID. NO. 3 or a functional fragment thereof. The nucleic acid molecule of the present invention can be incorporated in a suitable vector or vector system while the vector preferably is an expression vector, in particular further comprising a regulatory element. The regulatory element directs in particular and preferably a tissue-specific expression. The scope of the current invention also belongs a genetically engineered host cell comprising the mentioned expression vector or vector present in a suitable expression system. The peptide and/or polypeptide of the invention may be used for the preparation of a medicament for the treatment of human or animal diseases such as skin diseases The peptide and/or polypeptide are extremely useful in the screening for compounds that modulate the biological activity of the peptide and/or polypeptide. Thus, the obtained compounds can be incorporated into a pharmaceutical preparation comprising in addition for instance the peptide and/or polypeptide and/or nucleic acid molecule according to the invention and suitable pharmaceutically acceptable excipients. In yet another aspect the invention features a transgenic animal harboring a nucleic acid molecule described above. In order to clarify various terms used in the current description the meaning thereof is further elaborated hereunder without being interpreted as a limitation of the scope of the invention.

BRIEF DESCRIPTION OF THE DRAWINGS

FIG. 1 depicts the sequence of murine and human caspase-14 sequences. and their relationship with the caspase family.

FIG. 9 is a comparison of murine and human caspase-14 sequences.

DETAILED DESCRIPTION OF THE INVENTION

Definitions

Figure 2:
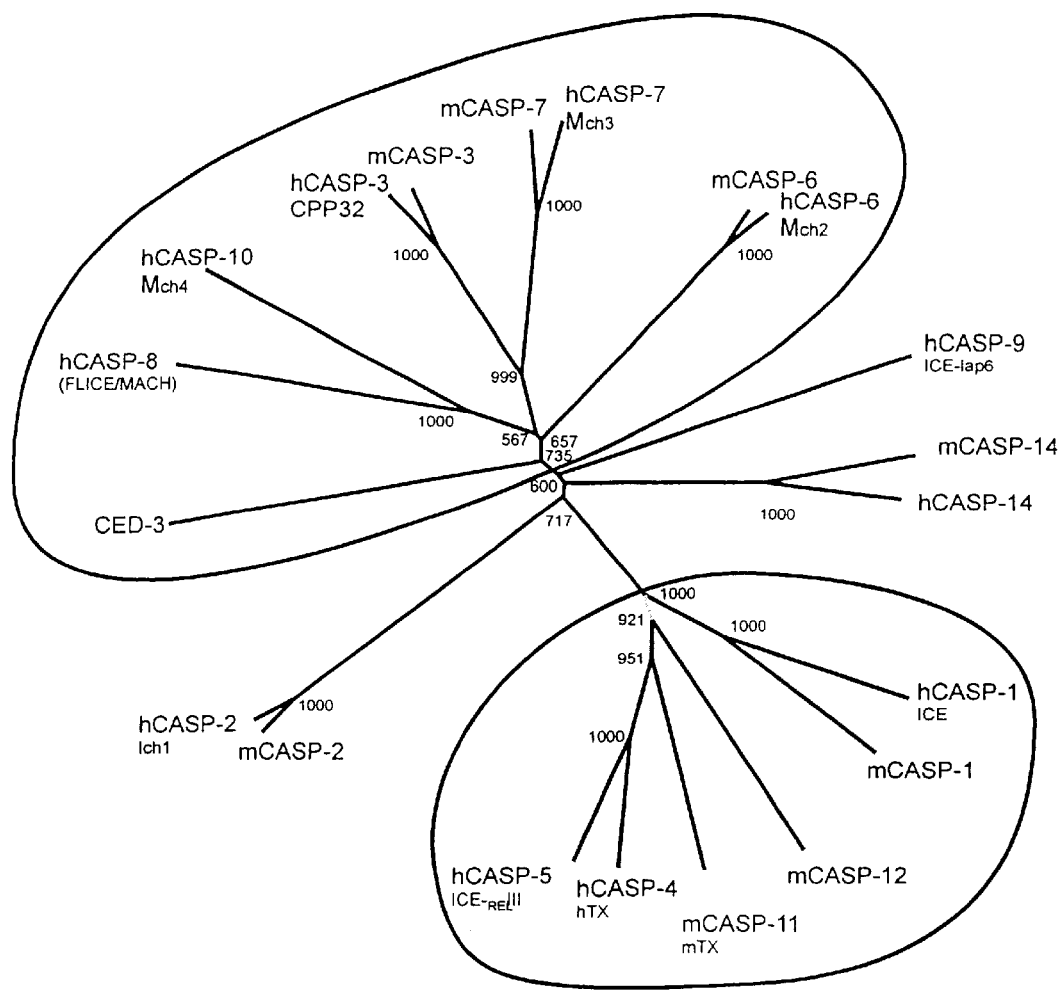
FIG. 2 illustrates murine and human caspase-14 sequences and their relationship with the caspase family.

"Nucleic acid" or "nucleic acid sequence" or "nucleic acid molecule" means genomic DNA, cDNA, double stranded or single stranded DNA, messenger RNA or any form of nucleic acid sequence known to a skilled person.

"Antibody" means polyclonal antibody, monoclonal antibody, single chain antibody, chimeric antibody, camilid antibody, diabody, heterodimeric or heteromultimeric antibody, immunotoxin or any molecule with a similar activity known to the people skilled in the art.

"Antigenic fragment" means any epitope of a protein against which antibodies can be raised. This fragment may be used as a purified peptide, or as an epitope in a larger protein, or it may be presented on an antigen presenting structure as known to the people skilled in the art.

"Specific probe" means any nucleic acid binding molecule, recognizing only or mainly (at least 60%) of the nucleic acid used as target sequence under the conditions used. Specific probes can be used for hybridization under different stringency conditions, or as primer for any nucleic acid sequence amplification technique such as the so-called polymeric chain reaction.

"Homology" in the context of amino acid sequences means identical or similar to the referenced sequence while obvious replacements/modifications of any of the amino acids provided, are included as well. A homology search in this respect can be performed with the BLAST-P (Basic Local Alignment Search Tool) program well known to a person skilled in the art.

For the corresponding nucleic acid sequence homology is referred to the BLASTX and BLASTN programs known in the art. Homology in this context means that the respective nucleic acid molecules or encoded proteins are functionally and/or structurally equivalent. The nucleic acid molecules that are homologous to the nucleic acid molecules described above and that are derivatives of the nucleic acid molecules are, for example, variations of the nucleic acid molecules which represent modifications having the same biological function, in particular encoding proteins with the same or substantially the same biological function. They may be naturally occurring variations, such as sequences from other varieties or species, or mutations. These mutations may occur naturally or may be obtained by mutagenesis techniques. The allelic variations may be naturally occurring allelic variants as well as synthetically produced or genetically engineered variants.

The proteins encoded by the various derivatives and variants of the above-described nucleic acid molecules have similar common characteristics, such as biological activity, molecular weight, immunological reactivity, conformation, etc., as well as physical properties, such as electrophoretic mobility, chromatographic behavior, sedimentation coefficients, pH optimum, temperature optimum, stability, solubility, spectroscopic properties, etc.

As mentioned, the present invention also relates to vectors, particularly plasmids, cosmids, viruses, bacteriophages and other vectors used conventionally in genetic engineering that contain a nucleic acid molecule according to the invention. Methods which are well known to those skilled in the art can be used to construct various plasmids and vectors; see, for example, the techniques described in Sambrook, Molecular Cloning A Laboratory Manual, Cold Spring Harbor Laboratory (1989) N.Y. Alternatively, the nucleic acid molecules and vectors of the invention can be reconstituted into liposomes for delivery to target cells. In a preferred embodiment, the nucleic acid molecule present in the vector is operably linked to (a) control sequence(s) which allow the expression of the nucleic acid molecule in prokaryotic and/or eukaryotic cells.

The term "control sequence" or "regulatory sequence" refers to regulatory DNA sequences which are necessary to affect the expression of coding sequences to which they are ligated. The nature of such control sequences differs depending upon the host organism. In prokaryotes, control sequences generally include promoter, ribosomal binding site, and terminators. In eukaryotes, control sequences include promoters, terminators and, in some instances, enhancers, transactivators or transcription factors. The term "control or regulatory sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is used.

Thus, the vector of the invention is preferably an expression vector. An "expression vector" is a construct that can be used to transform a selected host cell and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotic and/or eukaryotic cells are well known to those skilled in the art. The present invention furthermore relates to host cells, genetically engineered, comprising a vector as described above or a nucleic acid molecule according to the invention wherein the nucleic acid molecule is foreign to the host cell.

By "foreign" it is meant that the nucleic acid molecule is either heterologous or homologous with respect to the host cell. Heterologous means derived from a cell or organism with a different genomic background. Homologous means the host cell is located in a different genomic environment than the naturally occurring counterpart of the nucleic acid molecule. This means that, if the nucleic acid molecule is homologous with respect to the host cell, it is not located in its natural location in the genome of the host cell, in particular it is surrounded by different genes. In this case the nucleic acid molecule may be either under the control of its own promoter or under the control of a heterologous promoter. The vector or nucleic acid molecule according to the invention which is present in the host cell may either be integrated into the genome of the host cell or it may be maintained in some form extrachromosomally. In this respect, it is also to be understood that the nucleic acid molecule of the invention can be used to restore or create a mutant gene via homologous recombination (Paszkowski (ed.), Homologous Recombination and Gene Silencing in Plants. Kluwer Academic Publishers (1994)). The host cell can be any prokaryotic or eukaryotic cell, such as bacterial, insect, fungal, plant or animal cells. Preferred fungal cells are, for example, those of the genus Saccharomyces, in particular those of the species S. cerevisiae. Another subject of the invention is a method for the preparation of the inventive proteins which comprises the cultivation of host cells according to the invention which, due to the presence of a vector or a nucleic acid molecule according to the invention, are able to express such a protein, under conditions which allow expression of the protein and recovering of the so-produced protein from the culture.

The term "expression" means the production of a protein or nucleotide sequence in the cell. However, the term also includes expression of the protein in a cell-free system. It includes transcription into an RNA product, post-transcriptional modification and/or translation to a protein product or polypeptide from a DNA encoding that product, as well as possible post-translational modifications. Depending on the specific constructs and conditions used, the protein may be recovered from the cells, from the culture medium or from both. For the person skilled in the art it is well known that it is not only possible to express a native protein but also to express the protein as fusion polypeptides or to add signal sequences directing the protein to specific compartments of the host cell, e.g., ensuring secretion of the peptide into the culture medium, etc. Furthermore, such a protein and fragments thereof can be chemically synthesized and/or modified according to standard methods.

The terms "protein" and "polypeptide" used in this application are interchangeable. "Polypeptide" refers to a polymer of amino acids (amino acid sequence) and does not refer to a specific length of the molecule. Thus peptides and oligopeptides are included within the definition of polypeptide. This term does also refer to or include post-translational modifications of the polypeptide, for example, glycosylations, acetylations, phosphorylation and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The present invention furthermore relates to proteins encoded by the nucleic acid molecules according to the invention or produced or obtained by the above-described methods, and to functional and/or immunologically active fragments of such proteins. The proteins and polypeptides of the present invention are not necessarily translated from a designated nucleic acid sequence; the polypeptides may be generated in any manner, including for example, chemical synthesis, or expression of a recombinant expression system, or isolation from a suitable viral system. The polypeptides may include one or more analogs of amino acids, phosphorylated amino acids or unnatural amino acids. Methods of inserting analogs of amino acids into a sequence are known in the art. The polypeptides may also include one or more labels, which are known to those skilled in the art. In this context, it is also understood that the proteins according to the invention may be further modified by conventional methods known in the art. By providing the proteins according to the present invention it is also possible to determine fragments which retain biological activity, namely the mature, processed form. This allows the construction of chimeric proteins and peptides comprising an amino sequence derived from the protein of the invention, which is crucial for its binding activity. The other functional amino acid sequences may be either physically linked by, e.g., chemical means to the proteins of the invention or may be fused by recombinant DNA techniques well known in the art.

The term "functional fragment of a sequence" or "functional part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 30 amino acids. It is usually desirable to select sequences of at least about 10, 12 or 15 amino acids, up to a maximum of about 20 or 25 amino acids.

Furthermore, folding simulations and computer redesign of structural motifs of the protein of the invention can be performed using appropriate computer programs (Olszewski, Proteins 25 (1996), 286–299; Hoffman, Comput. Appl. Biosci. 11 (1995), 675–679). Computer modeling of protein folding can be used for the conformational and energetic analysis of detailed peptide and protein models (Monge, J. Mol. Biol. 247 (1995), 995–1012; Renouf, Adv. Exp. Med. Biol. 376 (1995), 37–45). In particular, the appropriate programs can be used for the identification of interactive sites of the inventive protein, its receptor, its ligand or other interacting proteins by computer assistant searches for complementary peptide sequences (Fassina, Immunomethods 5 (1994), 114–120. Further appropriate computer systems for the design of protein and peptides are described in the prior art, for example in Berry, Biochem. Soc. Trans. 22 (1994),1033–1036; Wodak, Ann. N. Y. Acad. Sci. 501 (1987), 1–13; Pabo, Biochemistry 25 (1986), 5987–5991. The results obtained from the above-described computer analysis can be used for, e.g., the preparation of peptidomimetics of the protein of the invention or fragments thereof. Such pseudopeptide analogues of the natural amino acid sequence of the protein may very efficiently mimic the parent protein (Benkirane, J. Biol. Chem. 271 (1996), 33218–33224). For example, incorporation of easily available achiral WW-amino acid residues into a protein of the invention or a fragment thereof results in the substitution of amide bonds by polymethylene units of an aliphatic chain, thereby providing a convenient strategy for constructing a peptidomimetic (Banerjee, Biopolymers 39 (1996), 769–777). Superactive peptidomimetic analogues of small peptide hormones in other systems are described in the prior art (Zhang, Biochem. Biophys. Res. Commun. 224 (1996), 327–331). Appropriate peptidomimetics of the protein of the present invention can also be identified by the synthesis of peptidomimetic combinatorial libraries through successive amide alkylation and testing the resulting compounds, e.g., for their binding and immunological properties. Methods for the generation and use of peptidomimetic combinatorial libraries are described in the prior art, for example in Ostresh, Methods in Enzymology 267 (1996),220–234 and Dorner, Bioorg. Med. Chem. 4(1996),709–715. Furthermore, a three-dimensional and/or crystallographic structure of the protein of the invention can be used for the design of peptidomimetic inhibitors of the biological activity of the protein of the invention (Rose, Biochemistry 35 (1996), 12933–12944; Rutenber, Bioorg. Med. Chem. 4 (1996), 1545–1558).

Furthermore, the present invention relates to antibodies specifically recognizing the protein(s) according to the invention or parts, i.e., specific fragments or epitopes, of such a protein. The antibodies of the invention can be used to identify and isolate other related proteins and genes in any organism. These antibodies can be monoclonal antibodies, polyclonal antibodies, camelid antibodies or synthetic antibodies as well as fragments of antibodies, such as Fab, Fv or scFv fragments etc. Monoclonal antibodies can be prepared, for example, by the techniques as originally described in Köhler and Milstein, Nature 256(1975),495, and Galfré, Meth. Enzymol. 73 (1981), 3, which comprise the fusion of mouse myeloma cells to spleen cells derived from immunized mammals. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. These antibodies can be used, for example, for the immunoprecipitation and immunolocalization of proteins according to the invention as well as for the monitoring of the synthesis of such proteins, for example, in recombinant organisms, and for the identification of compounds interacting with the protein according to the invention. For example, surface plasmon resonance as employed in the BIAcore system can be used to increase the efficiency of phage antibodies selections, yielding a high increment of affinity from a single library of phage antibodies which bind to an epitope of the protein of the invention (Schier, Human Antibodies Hybridomas 7 (1996), 97–105; Malmborg, J. Immunol. Methods 183 (1995), 7–13). In many cases, the binding phenomena of antibodies to antigens is equivalent to other ligand/anti-ligand binding.

The invention also relates to a diagnostic composition comprising at least one of the aforementioned nucleic acid molecules, vectors, proteins, antibodies or compounds and optionally suitable means for detection. The diagnostic compositions may be used for methods for detecting expression of related proteins as described in the current invention by detecting the presence of the corresponding mRNA which comprises isolation of mRNA from a cell and contacting the mRNA so obtained with a probe comprising a nucleic acid probe as described above under hybridizing conditions, detecting the presence of mRNA hybridized to the probe, and thereby detecting the expression of the protein in the cell. Further methods of detecting the presence of a protein according to the present invention comprise immunotechniques well known in the art. One such example is an enzyme linked immunosorbent assay.

The terms "gene(s)," "polynucleotide," "nucleic acid sequence," "nucleotide sequence," "DNA sequence" or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog. Preferably, the DNA sequence of the invention comprises a coding sequence for the above defined caspase protein(s) according to the invention.

"coding sequence" is a nucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

By "transgenic animal" is meant any animal containing cells that bear genetic information received, directly or indirectly, by deliberate genetic manipulation at the subcellular level, such as DNA received by microinjection or by infection with recombinant virus. Thus, animals of the invention are those with one or more cells that contain a recombinant DNA molecule of the invention and, in this context, the term "animal" denotes all animals except *Homo sapiens*. Farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats) are especially preferred. It is also preferred that the nucleic acid molecule becomes integrated with the animal's chromosomes, but the use of DNA sequences that replicate extrachromosomally, such as might be engineered into yeast artificial chromosomes, is also contemplated.

The term "transgenic animal" also includes animals in which the genetic information has been taken up and integrated into a germ line cell. These animals typically have the ability to transfer the genetic information to their offspring. If the offspring in fact possess some or all of the genetic information delivered to the parent animal, then they, too, are transgenic animals.

As used herein, the term "composition" refers to any composition such as a pharmaceutical composition comprising as an active ingredient an isolated functional protein according to the present invention possibly in the presence of suitable excipients known to the skilled man and may thus be administered in the form of any suitable composition as detailed below by any suitable method of administration within the knowledge of a skilled man. The preferred route of administration is parenterally. In parenteral administration, the compositions of this invention will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives.

The isolated functional protein of the invention is administered at a concentration that is therapeutically effective to treat a disease, more preferably a skin disease. The dosage and mode of administration will depend on the individual. Generally, the compositions are administered so that the isolated functional protein is given at a dose between 1 mg/kg and 10 mg/kg, more preferably between 10 mg/kg and 5 mg/kg, most preferably between 0.1 and 2 mg/kg. Preferably, it is given as a bolus dose. Continuous short time infusion (during 30 minutes) may also be used. The compositions comprising the isolated functional protein according to the invention may be infused at a dose between 5 and 20 mg/kg/minute, more preferably between 7 and 15 mg/kg/minute.

According to a specific case, the "therapeutically effective amount" of the isolated functional protein according to the invention needed should be determined as being the amount sufficient to cure the patient in need of treatment or at least to partially arrest the disease and its complications. Amounts effective for such use will depend on the severity of the disease and the general state of the patient's health. Single or multiple administrations may be required depending on the dosage and frequency as required and tolerated by the patient.

Fragment (of polypeptide) means every peptide or polypeptide derived from a bigger polypeptide by digestion, chemical modification, chemical or biochemical synthesis, or another method known to the people skilled in the art, whereby the peptide or polypeptide is carrying a relevant biological function such as enzymatic activity or the presence of an epitope, either as fragment alone or as a mixture of at least two fragments.

Fragment (of nucleic acid) means every oligo- or polynucleotide that encodes a fragment of a polypeptide and/or can be used as a specific probe for hybridization and/or can be used as a specific primer for a nucleic acid amplification reaction such as the so-called PCR reaction.

Compound means any chemical or biological compound, including simple or complex inorganic or organic molecules, peptides, peptido-mimetics, proteins, antibodies, carbohydrates and nucleic acids, that interferes with the synthesis and/or biological activity of the new members of the caspase family.

EXAMPLES

Example 1

Identification of a New Murine Caspase

In order to identify new murine caspases, TBLASTN searches for homology with known human caspases were performed on an expressed sequence tag (EST) database. Two new murine cDNA clones with significant caspase homology were identified: clones 555962 and 607978. The physical cDNA clones were obtained from the I.M.A.G.E. consortium (Washington University School of Medicine, St. Louis, Mo.; Lennon et al, 1996).

Clone 555962 was used as a template to amplify caspase-14 with the PCR primers GCGAAGCTTCCACCATG-GAGTCAGAGATGAGTGATCCT (SEQ. ID. NO. 5) and GGGAGAAGCGGCCGCTTGCAAATAGAGCTTCTTCC (SEQ. ID. NO. 6). The HindIII/NotI-digested amplicon was provided with a C-terminal E-tag in a modified pCDNAI vector (Invitrogen, San Diego, Calif.) to generate pCDNA-mCASP-14E. To construct pCAG-mCASP-14, murine caspase-14 was amplified with the primers GCGGATATC-CACCATGGAGTCAGAGATGAGTGATCCT (SEQ. ID. NO. 7) and GCGGATATCTTATTGCAAATAGAGCT-TCTTCC (SEQ. ID. NO. 8). Then the EcoRV-digested amplicon was ligated in a BalI-opened pCAGGS expression vector (Niwa et al, 1991). The cowpox CrmA gene (a generous gift from Dr. D. Pickup, Durham, N.C.) was EcoRI-cloned in pCAGGS, resulting in pCAG-CrmA.

Figure 1:
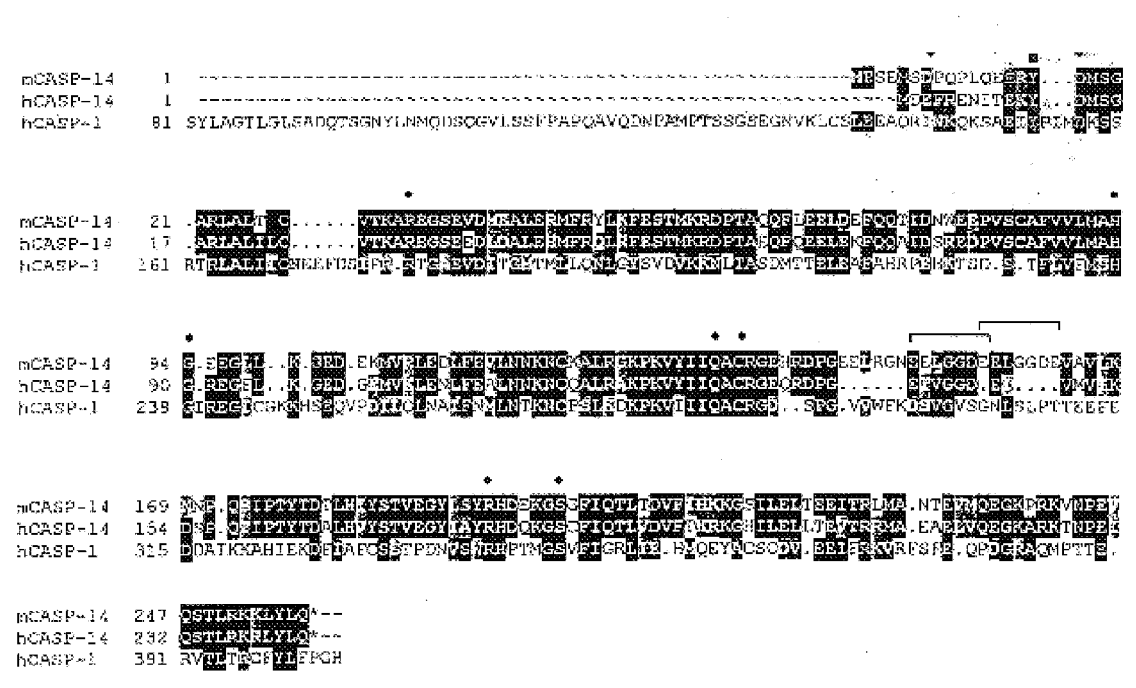

Sequencing of these cDNA clones on an ABI373A sequencer (Applied Biosystems, Foster City, Calif.) revealed that both encode the same open reading frame and contained an in-frame stop codon 5' of the start codon. This suggests that these cDNAs span the full open reading frame (SEQ. ID. NO. 1). Considering that the prodomain of caspases is removed from the p20 subunit by cleavage after Asp, murine caspase-14 contains at most a prodomain of only 7 ($D_7$) or 17 ($D_{17}$) amino acids. However, based on multiple sequence alignment the Tyr residue at position 16 ($Y_{16}$) is conserved in the large subunit of all known mammalian caspases. Therefore if there is indeed a prodomain, $D_7$ is the most likely to define it. Three Asp residues ($D_{142}$, $D_{156}$ and $D_{162}$) are potential cleavage sites between a p18 and a p11 subunit. $His_{93}$, $Gly_{94}$ and $Cys_{136}$, homologous to the catalytically important residues of human caspase-1, are conserved (Walker et al, 1994; Wilson et al, 1994) (FIG. 1). The amino acids $Arg_{33}$, $Gln_{134}$, $Arg_{294}$ and $Ser_{200}$, constituting the Asp-binding pocket, are the same as in human caspase-1 (Walker et al, 1994; Wilson et al, 1994) (FIG. 1) and other murine and human caspases (Van de Craen et al, 1997a). These features suggest that murine caspase-14, like caspase-1, exerts a cysteine protease activity upon activation. FIG. 2 shows that murine caspase-14 is relatively more related to human caspase-9 and human/murine caspase-2, and that it is not a member of the caspase-3 or caspase-1 subfamilies. This suggests that, besides the well-defined caspase-1 and caspase-3 subfamilies, a third group of proteins (human caspase-9, human/murine caspase-2 and murine caspase-14) is emerging, with relatively low homology to each other. Therefore, it is doubtful whether they can be considered one subfamily.

Figure 3:
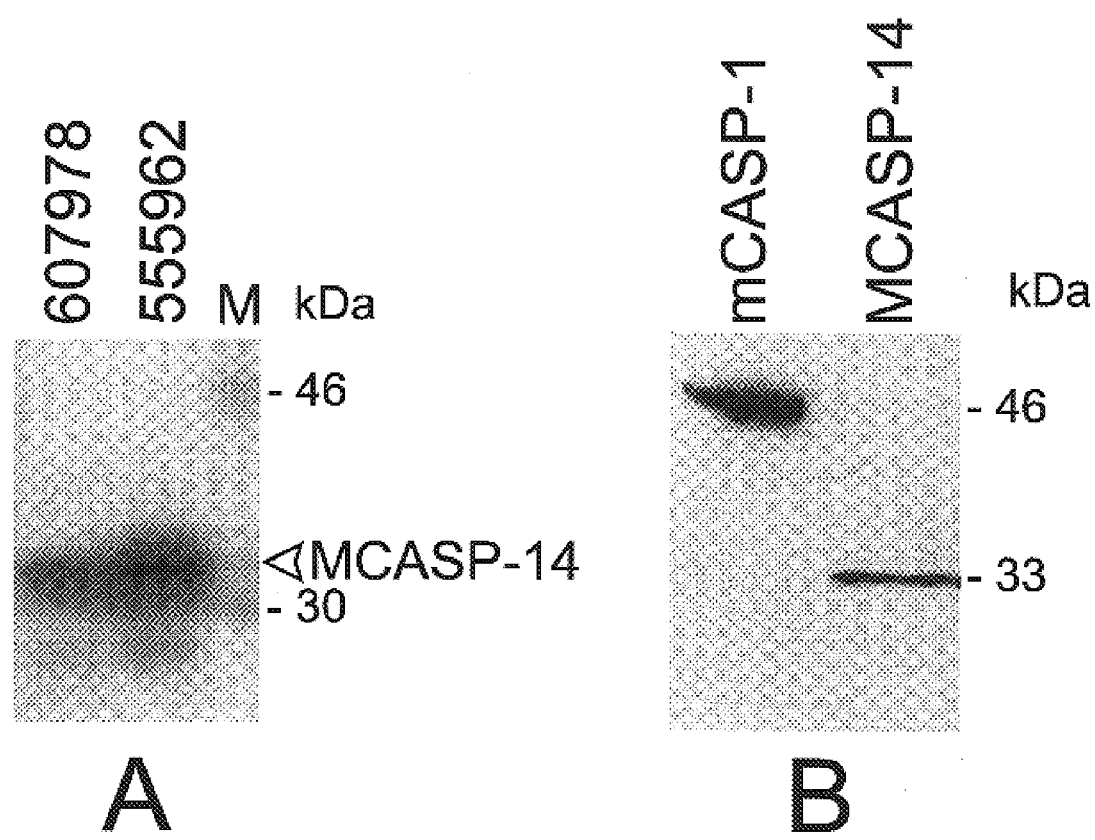
FIG. 3A is an SDS-polyacrylamide del determining the polypeptide length verification of murine caspase-14.
FIG. 3B depicts HEK293T cells that were transiently transfected with E-tagged murine caspase-1 or murine caspase-14.

More specifically, FIG. 1 illustrates the analysis of murine and human caspase-14 sequences and their relationship with the caspase family. FIG. 1 shows the alignment of the amino acid sequence of murine and human caspase-14 with human caspase-1. Identical and similar amino acids are boxed in black and gray, respectively. FIG. 1 shows the amino acids aligning with the residues in human caspase-1 which form the binding pocket for P1 Asp., indicated by a "♦" amino acids involved in catalysis are indicated by a "●" and $Y_{16}$, indicated by a "■," believed to belong to the p18 subunit. $D_7$ and $D_{17}$, indicated by a "▲," define a putative prodomain and a less likely alternative, respectively. Brackets indicate both EELGGDE heptapeptides containing the presumed cleavage sites between p18 and p11 subunits. FIG. 2 illustrates the phylogenetic comparison of human and murine caspases. More specifically, FIG. 2 illustrates the polypeptide length verification of murine caspase-14. The amino acid sequences were aligned using the Genetics Computer Group (Madison, Wis.) PILEUP algorithm (gap weight=3.0; gap length weight=0.1). This alignment was inserted into the CLUSTAL W program (Thompson, et at, 1994) to generate the dendrogram. Bootstrap values are indicated at the fork of each branch. The well-defined caspase-1 and caspase-3 subfamily members are circled. Note that murine caspase-11 is presumably the homologue of human caspase-4 (TX) (Van de Craen, et al., 1 997a). FIG. 3A shows the in vitro transcription and translation of murine caspase-14 clones in reticulocyte lysate in the presence of $^{35}$S-methionine for 90 mm at 30° C. 1 ml of this mixture was loaded on a 15% SDS-polyacrylamide gel. Molecular weight markers are shown in the lane marked "M." FIG. 3B illustrates detection of E-tagged caspase-14 in HEK293T lysates. HEK293T cells were transiently transfected with E-tagged murine caspase-1 or murine caspase-14. The lysates were prepared 30 h later, fractionated by SDS-PAGE, electroblotted and revealed with an anti-E-tag antibody.

In order to verify whether the length of the theoretical open reading frame corresponds with the $M_r$ of the protein coded for by the cDNA, both clones 607978 and 555962 were in vitro transcribed and translated in the presence of $^{35}$S-methionine. The resulting products were analyzed on 15% SDS-PAGE. As shown in FIG. 3A, both murine caspase-14 encoding clones generated a product of approximately 31 kDa (the theoretical calculated $M_r$ is 29.5 kDa), indicating that the presumed start codon is used. In order to confirm that murine caspase-14 is correctly expressed in eukaryotic cells, it was elongated at its C-terminus with an E-tag (pCDNA-mCASP-13E). 1 µg of this expression plasmid was transiently transfected in 5×10$^5$ HEK293T cells per well in a 6 well plate using the calcium phosphate method (O'Mahony and Adams, 1994). HEK293T is a human embryonal kidney carcinoma stably transfected with the SV40 T-antigen, having a transfection efficiency of >40% (a generous gift of Dr. M. Hall, University of Birmingham, UK; DuBridge et al, 1987). E-tagged murine caspase-1 expression was included as a positive control. As expected, murine caspase-14 and murine caspase-1 were expressed as proteins of 33 kDa and 46 kDa, respectively (FIG. 3B).

Example 2

Isolation of Human Caspase-14

Using BLASTN, a human genomic sequence was detected that was partly homologous to the murine sequence. Based on the murine sequence, using Genscan to determine the intron-exon boundaries, the human sequence was deduced, as depicted in SEQ.ID.NO. 3. Based on the predicted sequence, the human caspase-14 gene is cloned and its sequence is confirmed.

Example 3

Expression Pattern of Murine Caspase-14

A multiple tissue Northern blot of eight different mouse adult tissues and a Northern blot containing poly(A)$^+$ RNA from four mouse embryos (7, 11, 15 and 17 days old) were purchased from Clontech Laboratories (Palo Alto, Calif.). Sequential hybridization and stripping were performed according to the manufacturer's instructions.

In two independent experiments this multiple adult tissue Northern blot was hybridized with the 1719 bp EcoRI fragment of clone 607978. No hybridization was observed with this caspase-14 probe (FIG. 4A). Afterwards, the quality of the blot was checked using a murine caspase-7 cDNA probe. A murine caspase-7 transcript of 2.5 kb was clearly detectable (FIG. 4A) and the expression pattern was similar to that found previously (Van de Craen et al 1997a). It can be concluded that murine caspase-14 transcripts, if any, were below the detection limit in the adult tissues examined. Since clone 555962 was isolated from a mouse embryo cDNA library, we examined whether murine caspase-14 mRNA was expressed in mouse embryos. A Northern blot was hybridized containing poly(A)$^+$ RNA from 7, 11, 15 and 17 days old, whole embryos (FIG. 4B). The murine caspase-14 probe clearly recognized a transcript of 2.5 kb. The murine caspase-14 mRNA expression increased during maturation of the embryo (FIG. 4B). Remarkably, the 11-day old embryo did not show expression of caspase-14 mRNA. Hybridization of the same blot with a caspase-3 or a caspase-8 probe suggests that all lanes contain equal amounts of poly(A)$^+$ RNA (FIG. 4B). Because the caspase-14 transcript size (which includes a large poly(A)$^+$ tail) was consistent with the length of both cDNA clones (2203 bp and 2213 bp), the latter presumably contained an insert corresponding to the major caspase-14 mRNA species. A weaker band was detected at 4.5 kb and possibly represents an incompletely or alternatively processed mRNA. Since clone 607978 was isolated from a mouse skin derived cDNA library, the expression of caspase-14 transcripts was examined in adult mouse skin by reverse transcriptase PCR (RT-PCR). Reverse transcriptase reactions on total RNA isolated from murine adult skin were performed by the superscript preamplification system for first strand cDNA synthesis (Gibco BRL,). The primers GCGGATATCTGAG-GTTGCTGTGCTCAAGAACAACC (SEQ. ID. NO. 9) and GCGGAATTCGATATCTTATTGCAAATA-GAGCTTCTTCC (SEQ. ID. NO. 10) were used to amplify a caspase-14 cDNA fragment of 331 bp, while the primers GCTCACCATGGATGATGATATCGCC (SEQ. ID. NO. 11) and GGATGCCTCTCTTGCTCTGGGCCTC (SEQ. ID. NO. 12) were applied for amplification of an actin cDNA fragment of 199 bp.

Figure 4:
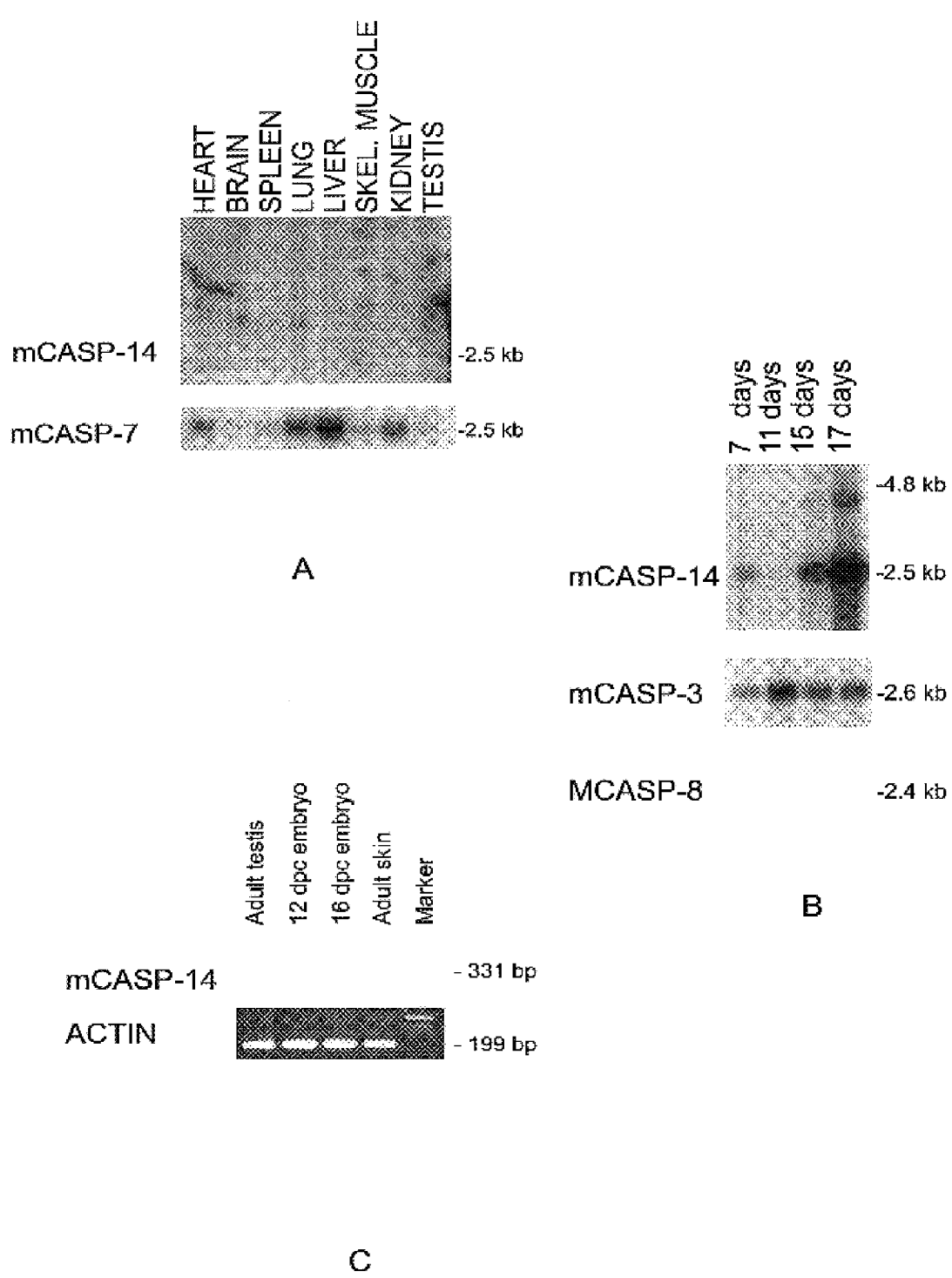
FIG. 4A depicts the expression pattern of murine caspase-14. Specifically, the figure illustrates mouse multiple tissue Northern blot hybridized sequentially with murine caspase-14 or murine caspase-7 cDNA. Each lane contains 2 mg poly(A)$^+$ RNA.
FIG. 4B depicts the expression pattern of murine caspase-14. Specifically, the figure shows whole mouse embryo Northern blot hybridized with murine caspase-14, -3 or -8 cDNA.
FIG. 4C depicts the expression pattern of murine caspase-14. Reverse transcriptase PCR on total RNA derived from murine adult testis, 12 dpc murine embryo, 16 dpc murine embryo and murine adult skin.

FIG. 4C demonstrates that a caspase-14 cDNA fragment can be amplified from RNA prepared from adult mouse skin (lane 4), while RT-PCR performed on RNA from adult mouse testis did not result in amplification of the caspase-14 cDNA fragment (lane 1). To confirm the apparent absence of caspase-14 transcripts around day 11 of development, additional amplifications were performed on RNA isolated from 12 dpc and 16 dpc mouse embryos, using the same PCR conditions as described above. Indeed, caspase-14 could be amplified from RNA derived from 16 dpc embryos but not from RNA derived from 12 dpc embryos (FIG. 4, lanes 2 and 3). Amplification of an actin cDNA fragment was identical for all RNA preparations (FIG. 4C). In summary, the expression of caspase-14 transcripts increases during maturation of a mouse embryo but drops temporally to an undetectable level around 11–12 dpc. Additionally, the expression pattern in adult tissues is very limited. Of the adult tissues examined, only in skin are caspase-14 transcripts are found. This tissue-specific expression in adult skin, as detected by Northern blotting, suggests an important role of the protein in skin physiology, such as homeostasis and/or keratinization. In fact, the process of keratinization of the skin epithelial cells can be considered as a well controlled way of incomplete cell death in which caspase-14 is considered to be crucial. This identifies this protein as a target to treat skin diseases.

Example 4

Murine Caspase-14 is a Weak Substrate of Caspase-8, but is no Substrate of Caspase-1, Caspase-2, Caspase-3, Caspase-6, Caspase-7, Caspase-11 or Granzyme B Members of the caspase family are activated by cleavage at Asp residues to generate p20 and p10 subunits which constitute the active tetrameric enzyme ($p20_2/p10_2$) (Nicholson et al, 1995; Walker et al 1994; Wilson et al 1994). Since proforms of caspases are often substrates for active $p20_2/p10_2$ caspases (Srinivasula et al, 1996) or granzyme B (Darnon et al, 1995; Van de Craen et al, 1997b), we examined whether caspase-14 was proteolytically cleaved by these prolteases. Radiolabeled $His_6$-tagged murine caspase-14 was obtained by in vitro transcription/translation of the pLT-mCASP-14 plasmid, as previously described for other caspases (Van de Craen et al., 1997a) and purified using a $Co^{+2}$ resin (Talon; Promega Biotec, Madison, Wis.). Radiolabeled caspase-14 was incubated with purified murine caspase-x (x=1, 2, 3, 6, 7 and 11) or purified murine granzyme B. However, none of the active enzyme preparations were able to cleave caspase-14.

Figure 5:
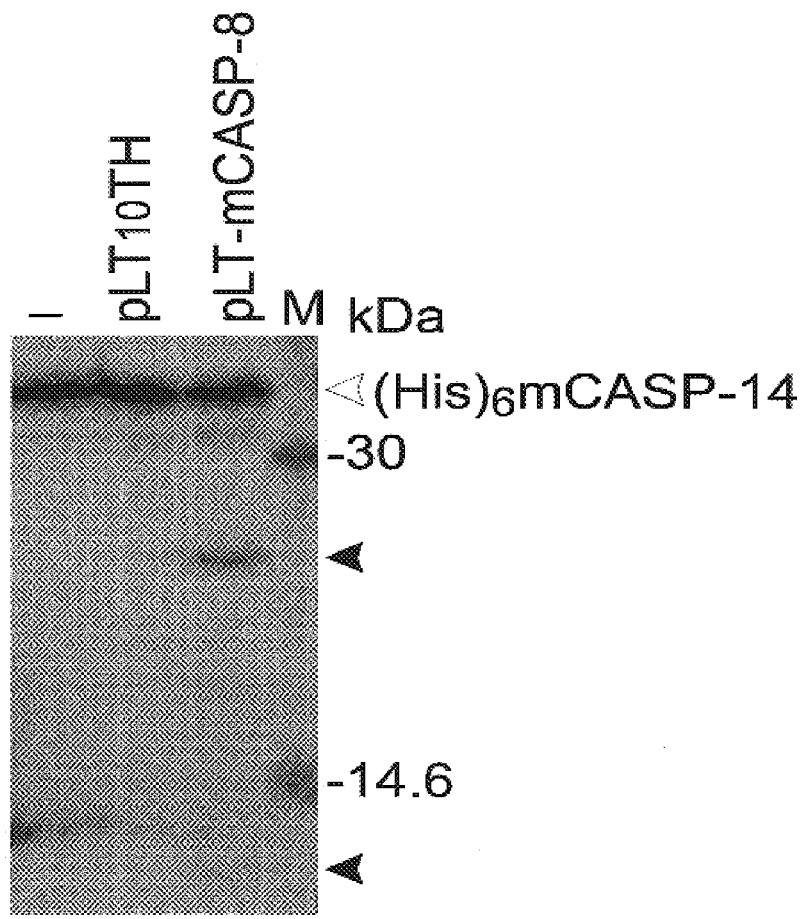
FIG. 5 depicts in vitro cleavage of $^{35}$S-methionine-labeled His$_6$-tagged murine caspase-14 by murine caspase-8.

Because purified, enzymatically active murine caspase-8 was not available, a lysate of *Escherichia coli*-expressing pLT-DpromCASP-8 was used to examine whether murine caspase-8 exhibited proteolytic activity on in vitro radiolabeled and partially purified $His_6$-tagged murine caspase-14 using $Co^{2+}$ resin chromatography and radiolabeled caspase-3 as a positive control for caspase-8 proteolytic activity. The proteolytic activity of murine caspase-8 was determined by making a 1/5 serial dilution of total lysate of murine caspase-8-expressing bacteria starting with 30 μg protein. These dilutions were incubated with 5 ml purified, radiolabeled, $His_6$-tagged caspase-14 or 1 ml radiolabeled caspase-3 in a total volume of 20 ml in caspase buffer (50 mM HEPES, pH 7.5, 10 mM DTT, 1 mM EDTA, 1 mM PMSF, 50 mM leupeptin and 20 mg/ml aprotinin) for 90 min at 37° C. The $His_6$-tagged murine caspase-14 migrated about 4 kDa slower on SDS-PAGE as compared to non-tagged caspase-14 (the epitope tag adds 2 kDa to the $M_r$, resulting in a theoretical 31.4 kDa). FIG. 5 shows that murine caspase-8 cleaved this 35.5 kDa murine caspase-14 weakly into 24 kDa (p18) and 11 kDa (p11) fragments. In vitro cleavage of $^{35}$S-methionine-labeled $His_6$-tagged murine caspase-14 by murine caspase-8 is shown. FIG. 5 shows 5 ml of in vitro labeled, purified $His_6$-tagged murine caspase-14 was incubated with 30 mg lysate of *Escherichia coli* transfected with pLT-mCASP-8 plasmid. Lysate of bacteria transfected with empty pLT10TH served as a control. The resulting cleavage products are shown underneath. Uncleaved products are indicated by open arrowheads; resulting cleavage fragments are shown by closed arrowheads. n, $His_6$ tag of 2 kDa; T, theoretically calculated $M_r$; Exp, experimentally found $M_r$. These products suggest cleavage at $D_{156}$ and/or $D_{162}$. Since these Asp residues are both embedded in an identical, repeated EELGGDE heptapeptide (FIG. 1), it is quite possible that cleavage occurs at both sites. It should be noted that the slower migration of the full-length $His_6$-tagged murine caspase-14 was largely due to the charged $His_6$ tag, since the p18 fragment also runs approximately 4 kDa slower than theoretically expected (FIG. 5).

Figure 6:
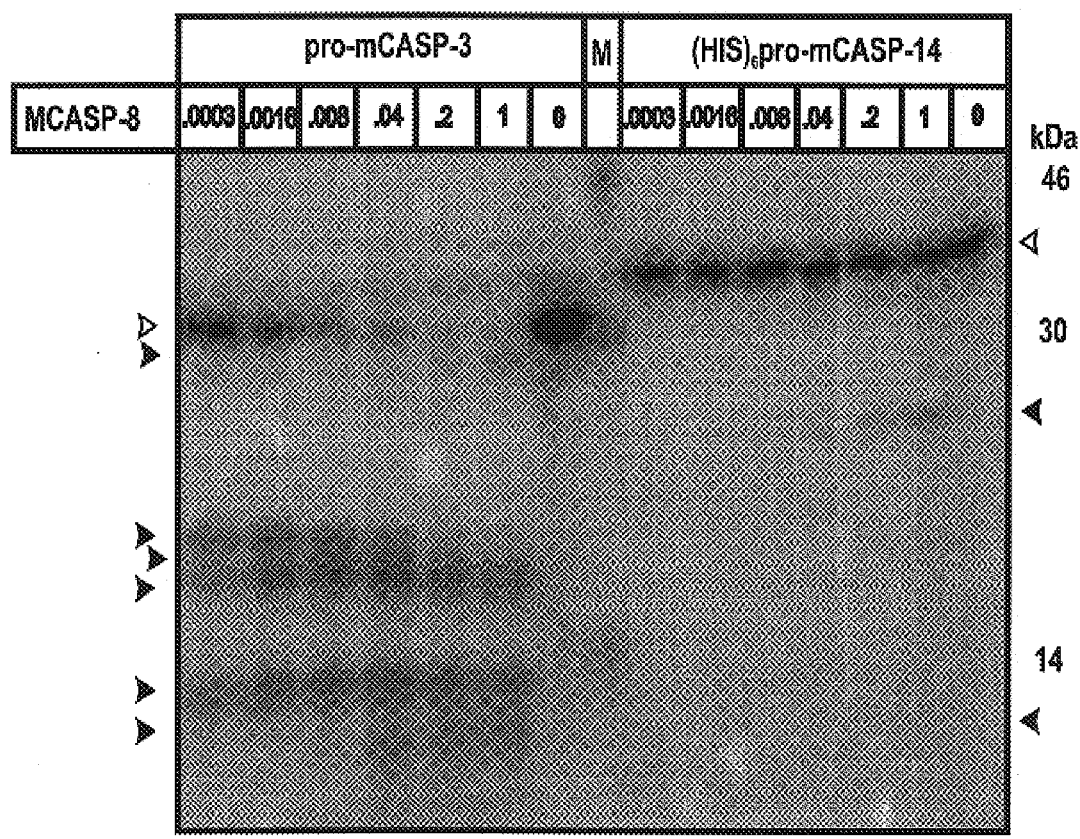
FIG. 6 depicts in vitro cleavage of $^{35}$S-methionine-labeled His$_6$-tagged murine caspase-14 by murine caspase-8.

To investigate the efficiency of caspase-8-mediated cleavage of caspase-14, the caspase-8 dependent proteolysis of radiolabeled $His_6$-tagged caspase-14 was compared with caspase-3 at the conditions described above. The resulting products were analyzed by SDS-PAGE and autoradiography. Thus, FIG. 6 shows a 1:5 serial dilution was made starting with 30 mg lysate of bacteria expressing pLT-mCASP-8 (=1). Each dilution was incubated with 5 ml of labeled, purified $His_6$-tagged murine caspase-14 or 1 ml of radiolabeled murine caspase-3. Reaction products were separated on 15% SDS-PAGE, followed by autoradiography to reveal cleavage fragments. Uncleaved products are indicated by open arrowheads; resulting cleavage fragments are shown by closed arrowheads. M, $M_r$ marker. Therefore, FIG. 6 clearly demonstrates that proteolytic activity of caspase-8 was at least 1000 times more efficient on caspase-3 than on murine caspase-14. Consequently, it is quite possible that other proteases may process murine caspase-14 more efficiently than caspase-8, or that caspase-14 activation involves unknown mechanisms.

Example 5

Bacterial Expression of Murine caspase-14

The bacterial expression vectors for caspase-14 were constructed by PCR with GCGGATATCCATGGAGTCA-GAGATGAGTGATCCT (F1)(SEQ. ID. NO. 13), GCG-GATATCACCTCAGCCATTGCAGGAGGAAAGA (F2) (SEQ. ID. NO. 14), GCGGATATCCATGTCAGGTGCCCGCCTG-GCCCTGACG (F3)(SEQ. ID. NO. 15) and GCGGAATTC-GATATCTTATTGCAAATAGAGCTTCTTCC (R)(SEQ. ID. NO. 16). Primers F1 and R amplified fill-length caspase-14, primers F2 and R created the putative prodomain-deleted $D_{1-7}$mCASP-14, and primers F3 and R amplified $D_{1-17}$mCASP-14. The products were EcoRV-cloned into a pLT10TH vector (Mertens et al, 1995), resulting in pLT-mCASP-14,pLT-$D_{1-7}$mCASP-14 and pLT-$D_{1-17}$mCASP-14, respectively. The caspase-14 inserts were N-terminally fused to a $His_6$ tag to facilitate purification. The same cloning strategy with the primers GCGGATATCCAGT-GAGTCACGGACTTCAGACAAAG (SEQ. ID. NO. 17) and GCGGATATCGAATTCTCATTAGGGAGG-GAAGAAGAGCTTC (SEQ. ID. NO. 18) (and EST clone 533745 as template DNA) was applied to generate the bacterial expression vector for prodomain-deleted murine caspase-8, viz. pLT-DpromCASP-8.

pLT10-mCASP-14, pLT-$D_{1-7}$CASP-14 and pLT-$D_{1-17}$CASP-14 were transformed in MC 1061 bacteria containing a pICA2 plasmid. A 50 ml Luria broth culture of $A_{600}$=0.5 was induced overnight with 1 mM IPTG at 20° C. The cells were harvested by centrifugation. MC1061 cell pellets were suspended in 1 ml bacterial lysis buffer (20 mM Tris-HCl pH 7.5, 10% glycerol, 1 mM oxidized glutathione, 1 mM PMSF, 50 mM leupeptin and 20 mg/ml aprotinin) and lysed by sonication. The soluble and insoluble fractions were separated by centrifugation for 20 min at 16,000×g. The expressed proteins were analyzed by 12.5% SDS-PAGE and Coomassie blue staining. The same procedure was followed for pLT-DpromCASP-8.

Bacterial expression of caspases lacking their prodomain (p30) usually results in the generation of p20 and p10 domains in the soluble fraction of the bacterial extract (Molineaux et al, 1993; Kamens et al, 1995). Three different pLT10TH constructs were made to generate active murine caspase-14 enzyme. One plasmid contained the full-length murine caspase-14 coding sequence (pLT-mCASP-14). Furthermore, two constructs were generated in which a putative prodomain was removed (pLT-$D_{1-7}$mCASP-14 and pLT-$D_{1-17}$CASP-14). To facilitate the purification of the proteins, an N-terminal polyhistidine sequence ($His_6$ tag) was fused to the murine caspase-14 sequences. The same conditions for bacterial expression were used as for the generation of other prodomain-deleted murine caspases. These conditions generated active caspase-1, caspase-2, caspase-3, caspase-6, caspase-7, caspase-8 and caspase-11. All caspase-14 constructs were well expressed, but the product was predominantly in insoluble inclusion bodies. No p18 or p11 subunits became detectable after bacterial expression, and neither in the soluble nor in the insoluble fractions was aspartase activity detected using the Ac-DEVD-AMC (100 mM), Ac-YVAD-AMC (100 mM) or z-VAD-AFC (100 mM) fluorogenic peptide caspase substrates; this was also the case after 30 min preincubation of the soluble fraction at 37° C., which might have allowed an autocatalytic generation of caspase activity (Ramage et al, 1995). Also denaturation and refolding of the insoluble fractions of murine caspase-14 or separate expression of the subunits did not generate activity on the fluorogenic tetrapeptide substrates.

Example 6
Murine caspase-14 does not Autoprocess in Yeast

Figure 7:
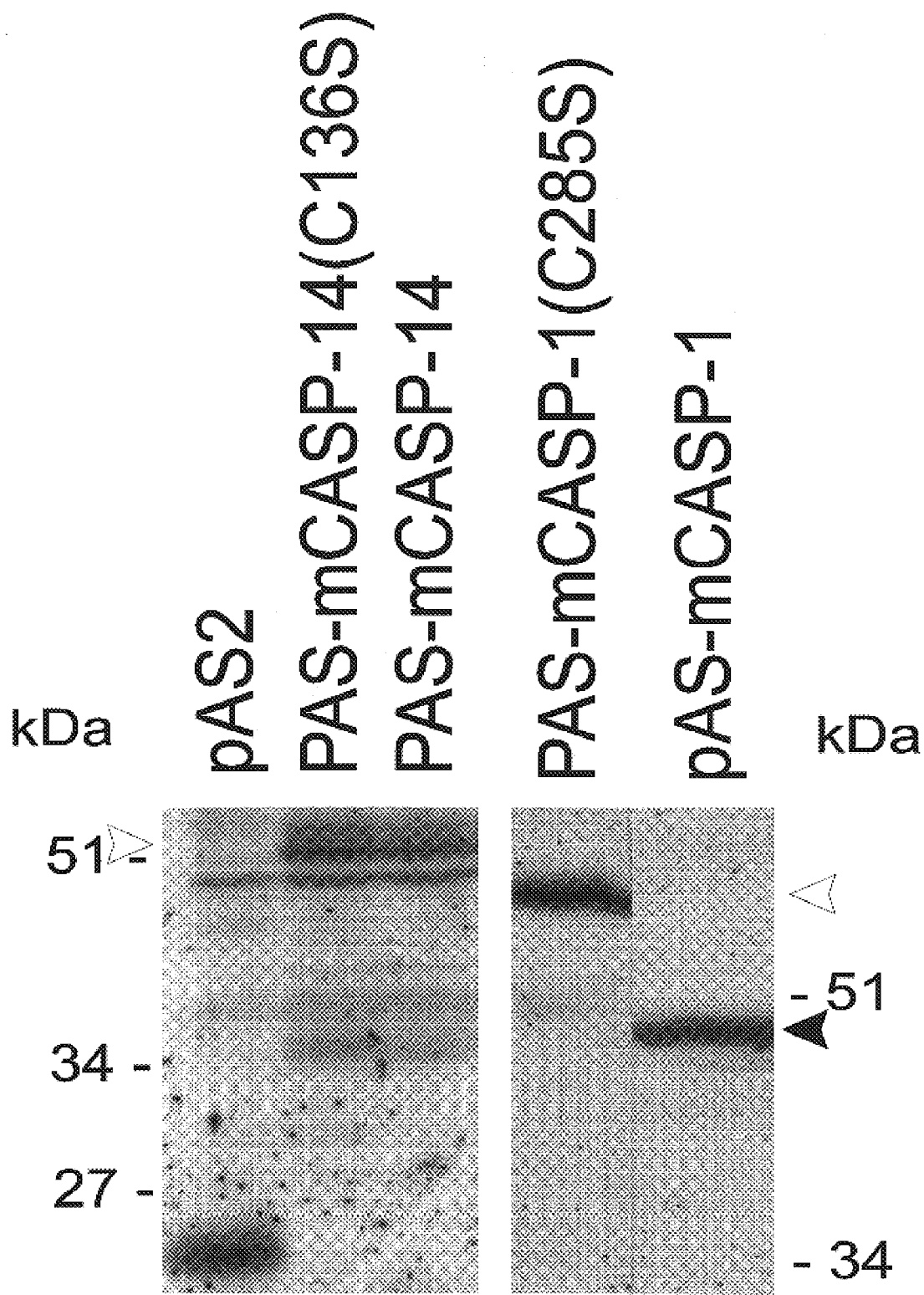
FIG. 7 is a gel illustrating that lysates of S. cerevisiae strain YRG-2, transformed with pAS2-encoding Gal4DB fusions with full-length murine caspase-1, murine caspase-1(C285S), murine caspase-14 or murine caspase-14 (C136S). In the lane at the right hand side, the cleavage product of the Gal4DB fusion with murine caspase-1 is derived from proteolysis at the C-terminal p10 domain of murine caspase-1.

Since bacterial expression of murine caspase-14 suggests the inability of this caspase to autoprocess, the autocleavage activity of murine caspase-14 was tested in a yeast expression system. Yeast murine caspase-14 expression plasmids were also constructed by PCR. The primers used were: AAAGAGATCGAATTCGCCATGGAGTCA-GAGATGAGTGATCCTC (YF)(SEQ. ID. NO. 19), ATA-GATCTCTGCAGGTCGACGTTATTG-CAAATAGAGCTTCTTCCGGAG (YR)(SEQ. ID. NO. 20), CATCCAGGCTAGTAGAGGAGGACACAGAG (YCSF)(SEQ. ID. NO. 21) and CTCTGTGCTCTCCTC-TACTAGCCTGGATG (YCSR)(SEQ. ID. NO. 22). Primers YF and YR were used to generate wild-type caspase-14. The four primers were applied to mutate the active Cys residue to Ser (C136S). All amplicons were NcoI/SalI-inserted in pAS2, to result in pASmCASP-14 and pASmCASP-14C136S. The Gal4DBp45ICE-C285S and the Gal4DBp45ICE plasmids (Van Criekinge et al 1996) were renamed pASmCASP-1C285 S and pASmCASP-1, respectively. Autocleavage in yeast was performed as previously described (Van Criekinge et al, 1996), except that the YRG-2 yeast strain (Stratagene Cloning Systems, La Jolla, Calif.) was used instead of HF7c.

pAS2 plasmids encoding the Gal4 DNA-binding domain (Gal4DB) fused with murine caspase-1, murine caspase-1C285S, murine caspase-14 or murine caspase-14C136S were transformed in *Saccharomyces cerevisiae* strain YRG-2. Single yeast colonies were used to prepare lysates for Western blot analysis with antibodies against Gal4DB. However, no autoprocessing activity could be detected for wild-type murine caspase-14 (FIG. 7). FIG. 7 illustrates that murine caspase-14 does not autoprocess in *Saccharomyces cerevisiae*. Lysates of *S. cerevisiae* strain YRG-2, transformed with pAS2-encoding Gal4DB fusions with full-length murine caspase-1, murine caspase-1(C285S), murine caspase-14 or murine caspase-14(C136S), were subjected to SDS-PAGE, electroblotted and revealed with anti-Gal4DB antibody. In the lane at the right hand side, the cleavage product of the Gal4DB fusion with murine caspase-1 is derived from proteolysis at the C-terminal p10 domain of murine caspase-1. Transformations with caspase-1 or the inactive Cys mutant of caspase-1 (CASP-1C285S) fused to Gal4DB were used as controls and confirmed that the p10 subunit of caspase-1 was cleaved off without involvement of endogenous yeast proteases (FIG. 7). These results indicate that murine caspase-14, in contrast to murine caspase-1, is not able to autoprocess in *Saccharomyces cerevisiae* which might contain eukaryotic helping factors. However, it should be kept in mind that caspase-14 contains no large prodomain that can be involved in oligomerization-induced autoactivation, as has been demonstrated for caspase-1 (Van Criekinge et al, 1996) and caspase-8 (Yang et al, 1998). Moreover, the question remains if induced dimerization would be able to generate activated caspase-14 fragments. It has been demonstrated that enforced dimerization of caspase-3 using a FK-BP/caspase fusion construct did not result in caspase-3 autoprocessing (Yang et al., 1998).

Example 7
Transiently Transfected caspase-14 Exhibits no Evident Apoptotic Related Activity in Mammalian Cells Cell lysates were prepared with lysis buffer containing 50 mM Tris pH 8.0, 300 mM NaCl, 5 mM EDTA, 15 mM $MgCl_2$, 1% NP40, 1 mM PMSF, 50 mM leupeptin and 20 mg/ml aprotinin. 90 mg of total protein was used for Western analysis with anti-E-tag antibody (Pharmacia Biotech, Uppsala, Sweden).

Figure 8:
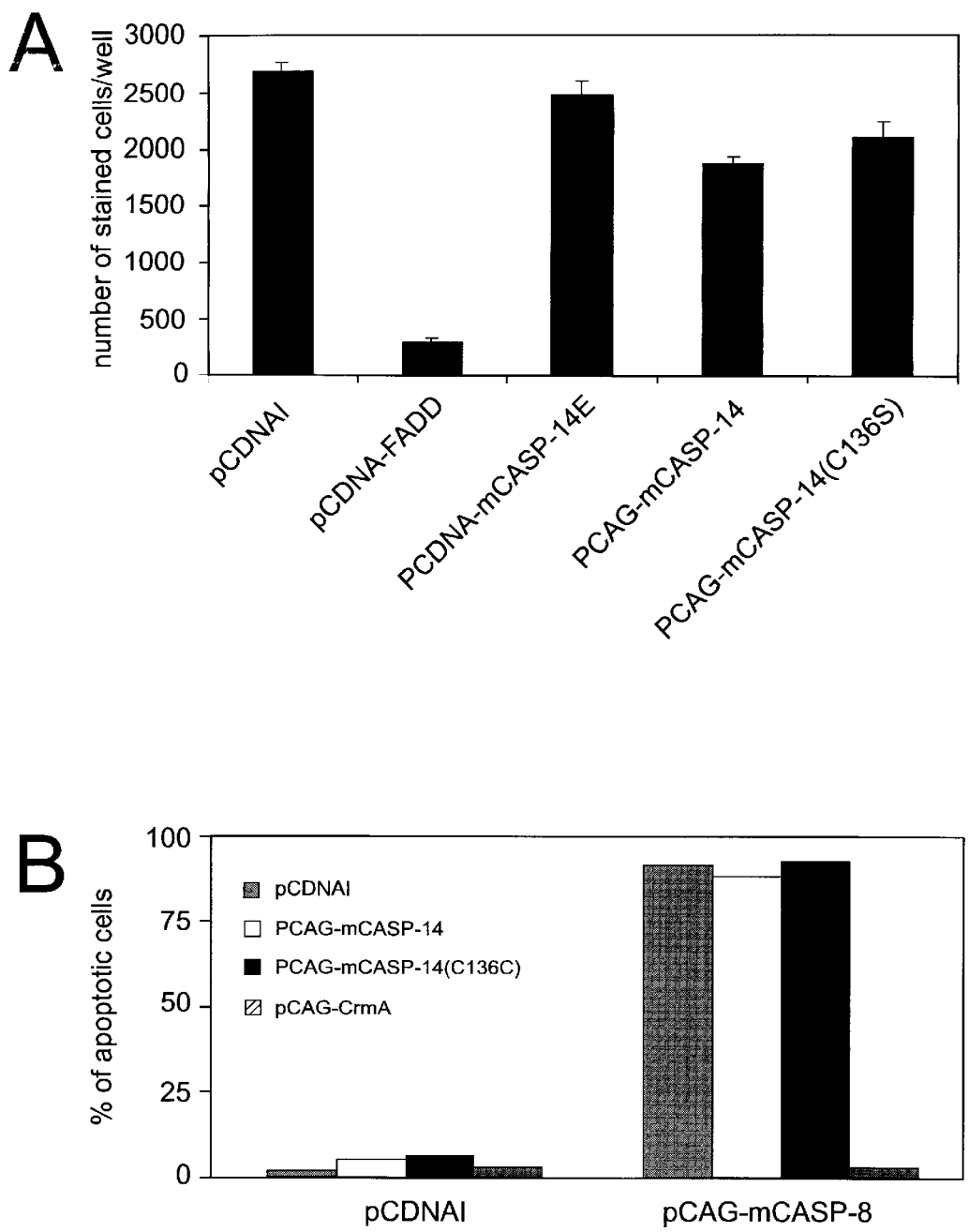
FIG. 8A is a graph comparing the number of stained cells of pCDNA-FADD, pCDNA-mCASP-14E, pCAG-mCASP-14, pCAG-mCASP-14(C136S) or empty pCDNAI.
FIG. 8B is a graph comparing the percentage of apoptotic cells of pCDNAI verses pCAG-mCASP-8.

In order to evaluate the apoptotic activity of caspases, $5 \times 10^5$ HeLaH21 cells per well in a 6-well plate were transiently transfected with DOPE transfection reagent according to the manufacturer's instructions (Eurogentec, Seraing, Belgium). HeLaH21 is a human cervix carcinoma derived from HeLa cells. A total of 2 mg DNA, 50% pUT651, a b-galactoside reporter gene construct (Cayla, Toulouse, France) and 50% vector of interest [pCAG-mCASP-14, pCAG-mCASP-14(C136S), pCDNA-mCASP-14E, pCDNA-FADD or empty pCDNAI vector] was used. After 24 h, the extent of cell death in the transfected population was measured by the decrease in the number of adherent, b-galactosidase-expressing cells as revealed using XGal substrate. This b-galactosidase assay was performed as described previously (Van de Craen et al, 1997a). A pCDNAI-derived expression vector coding for FADD was used as a positive control. FIG. 8A shows that transient overexpression of the FADD-containing plasmid caused profound reduction in the number of bbgalactosidase-expressing HeLaH21 cells as compared to the negative control (pCDNAI). Transient overexpression of the different murine caspase-14-encoding constructs did not result in a clear reduction in the number of adherent blue cells (FIG. 8A), suggesting that murine caspase-14 itself is not capable to induce apoptosis. Similar results were obtained in HEK293T cells.

With $FLIP_L$(Irmler et al, 1997) as an example, it is conceivable that caspase-14 exerts apoptosis inhibiting features. Another link to a potential caspase-14 interfering activity is the low protease activity of caspase-8 on caspase-14 as revealed by in vitro cleavage assays. Since Western blot analysis revealed that murine caspase-14 is well expressed in HEK293T cells, and since murine caspase-8 induced very clear apoptosis in this cell line, the potential effect of murine caspase-14 on murine caspase-8-induced apoptosis was examined in HEK293T cells by transient cotransfection experiments.

In order to assay the effect of murine caspase-14 on murine caspase-8-induced apoptosis, $5 \times 10^5$ HEK293T cells per well in a 6-well plate were transiently transfected using the calcium phosphate precipitation method (O'Mahoney and Adams, 1994). Three plasmids were transfected simultaneously: 200 ng pUT651, 50 ng pCDNA-mCASP-8 (which contains full-length murine caspase-8) and 600 ng pCAG-mCASP-14, pCAG-mCASP-14(C136S), pCAG-CrmA, or empty pCDNAI. Controls included experiments with empty pCDNAI instead of pCDNA-mCASP-8. Cotransfection of caspase-8 with CrmA was applied as a control for inhibition. FIG. 8B demonstrates that caspase-8-induced cell death was not influenced by cotransfection with caspase-14 or caspase-14(C136S), while CrmA inhibited cell death significantly. Also, dilution series of a murine caspase-8-encoding plasmid, cotransfected with caspase-14-expressing constructs, did not reveal any effect of caspase-14. These data indicate that caspase-14 does not interfere negatively with apoptosis, at least when cell death is induced by caspase-8. In FIG. 8B HEK293T cells were transfected with 200 ng pUT651 (for visualization of transfected cells), 50 ng pCDNA-mCASP-8 (for induction of cell death) and 600 ng pCAG-mCASP-14, pCAG-mCASP-14(C136S), pCAG-CrmA or empty pCDNAI. Controls included experiments with 50 ng pCDNAI instead of pCDNA-mCASP-8. After 24 h, cells were stained with XGal. Since HEK293T cells were very efficiently transfected, the percentage of blue apoptotic cells was determined.

Other Examples

FIG. 9 is an analysis of murine and human caspase-14 sequences. Alignment of sequences as performed by the MultiAlin software ("Multiple sequence alignment with hierarchical clustering" F. CORPET, 1988, Nucl. Acids Res., 16 (22), 10881–10890). Consensus sequences involved in catalysis are underlined, t possible cleavage sites between putative prodomain and p18 subunits or between p18 and p11 subunits, k amino acids aligning with the residues in human caspase-1 which form the binding pocket for P1 Asp.

Figure 10:
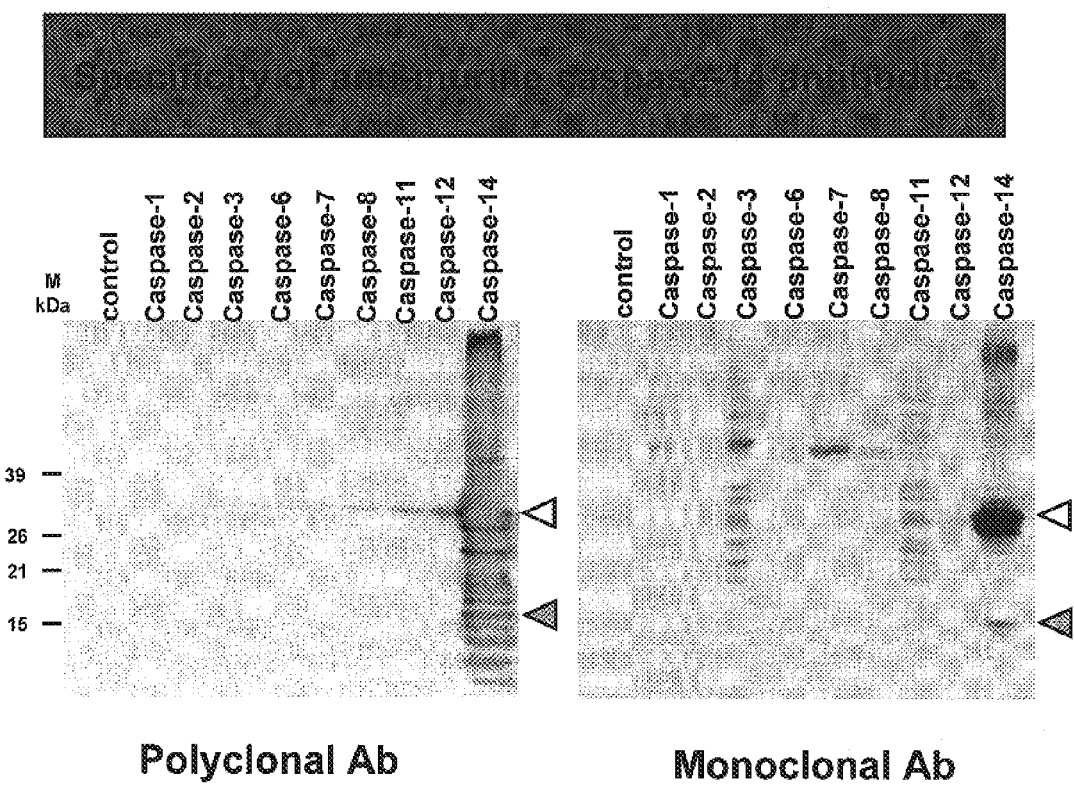
FIG. 10 depicts the western blot analysis of the immunoreactivity of rabbit polyclonal and mouse monoclonal 14-1-148 (1). It looks at the specificity of anti-murine caspase-14 antibodies.

FIG. 10 is a western blot analysis of the immunoreactivity of rabbit polyclonal and mouse monoclonal 14-1-148 (1). To determine the specificity of immunoreactivity the different antibodies were tested against a series of murine caspases. Different murine caspases were transiently expressed in HEK293T cells, lysed and 50 mg of total protein was loaded on an SDS-PAGE and electroblotted. Blots were developed using rabbit polyclonal or mouse monoclonal 14-1-148 anti-caspase-14 antibodies using ECL. Open arrows indicate caspase-14 proform, closed arrows indicate the processed p18 subunit. None of the aspecific bands showing up in lanes other than caspase-14 can be attributed to caspase fragments.

Figure 11:
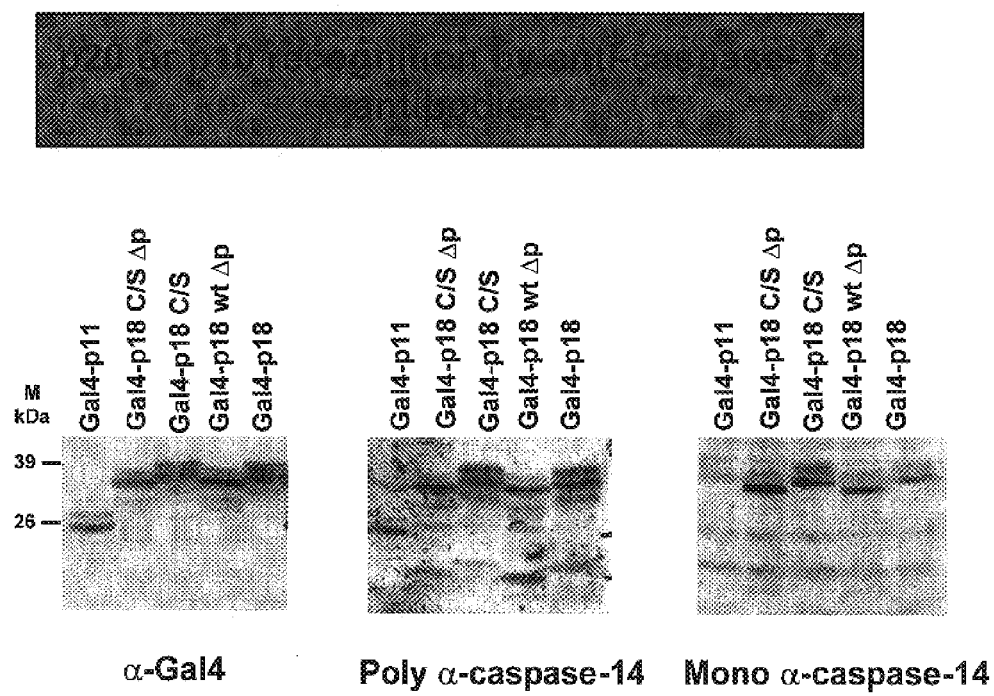
FIG. 11 depicts the western blot analysis of the immunoreactivity of rabbit polyclonal and mouse monoclonal 14-1-148 (2). It contains gels of p20 or p10 recognition by anti-caspase-14 antibodies.

FIG. 11 is a western blot analysis of the immunoreactivity of rabbit polyclonal and mouse monoclonal 14-1-148 (2). To determine the immunoreactivity to the different caspase-14 subunits (prodomain, p18 or p11) the different antibodies were tested against fusion proteins between the DNA binding domain (BD) of the yeast GAL4 protein and murine caspase-14 subunits.

Gal4-p11: Gal4BD fused to aa E163-end of murine caspase-14

Gal4-p18 C/S Dp: Gal4BD fused to aa M18-D155 of murine caspase-14, C136 mutated to Gal4-p18 C/S: Gal4BD fused to M1-D155 of murine caspase-14, C136 mutated to S Gal4-p18 wt Dp: Gal4BD fused to M18-D155 of murine caspase-14

Gal4-p18 wt: Gal4BD fused to M1-D155 of murine caspase-14

These constructs were cloned in pAS2 and pAS3 yeast expression plasmids and expressed in the yeast strain YRG-2 (Stratagene),equal amounts of yeast lysate were loaded on an SDS-PAGE and electroblotted. Blots were developed using rabbit polyclonal or mouse monoclonal 14-1-148 anti-caspase-14 antibodies or a anti-Gal4 antibody using ECL.

Figure 12:
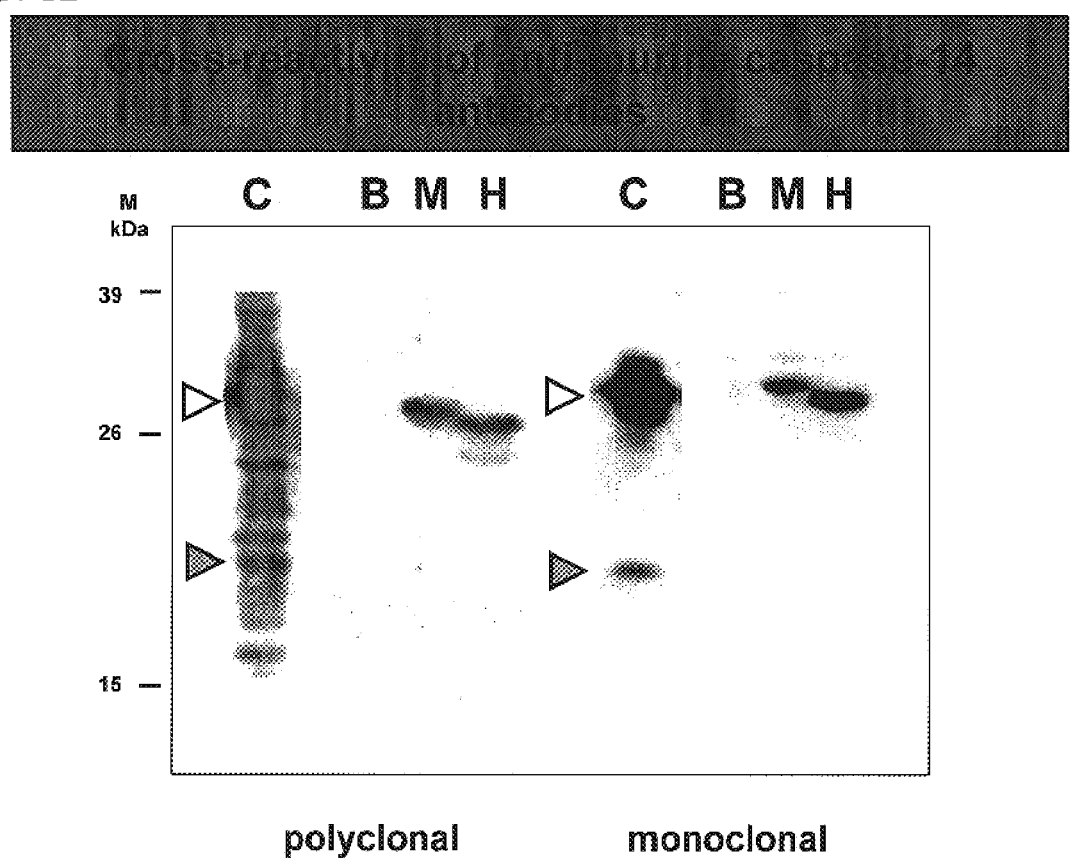
FIG. 12 depicts the western blot analysis of the immunoreactivity of rabbit polyclonal and mouse monoclonal 14-1-148 (3). It depicts the cross-reactivity of anti-murine caspase-14 antibodies.

FIG. 12 is a western blot analysis of the immunoreactivity of rabbit polyclonal and mouse monoclonal 14-1-148 (3). To determine the species cross-reactivity of the different antibodies, these were tested against a murine and human caspase-14. Therefore murine and human caspase-14 were transiently expressed in HEK293T cells, lysed and 50 mg of total protein was loaded on an SDS-PAGE and electroblotted. Blots were developed using rabbit polyclonal or mouse monoclonal 14-1-148 anti-caspase-14 antibodies using ECL. Open arrows indicate caspase-14 proform, closed arrows indicate the processed p18 subunit. C: control lysate of murine caspase-14 transfected HEK293T cells, B: transfection with empty vector, M: transfection with murine caspase-14 expressing plasmid, H: transfection with human caspase-14 expressing plasmid.

References

Bertin J, Armstrong R C, Ottilie S, Martin D A, Wang Y, Banks S, Wang G-H, Senkevich T G, Alnemri E S, Moss B, Lenardo M J, Tomaselli K J, Cohen J I (1997) Death effector domain-containing herpesvirus and poxvirus proteins inhibit both Fas- and TNFR1-induced apoptosis. Proc. Natl. Acad. Sci. USA 94: 1172–1176.

Boldin M P, Goncharov T M, Goltsev Y V, Wallach D (1996) Involvement of MACH, a novel MORT1/FADD-interacting protease, in Fas/APO-1- and TNF receptor-induced cell death Cell 85: 803–815.

Darmon A J, Nicholson D W, Bleackley R C (1995) Activation of the apoptotic protease CPP32 by cytotoxic T-cell-derived granzyme B Nature 377: 446–448.

DuBridge R B, Tang P, Hsia H C, Leong P-M, Miller J H, Calos M P (1987) Analysis of mutation in human cells by using an Epstein-Barr virus shuttle system. Mol. Cell. Biol. 7: 379–387.

Irmler M, Thome M, Hahne M, Schneider P, Hofmann K, Steiner V, Bodmer J-L, Schröter M, Burns K, Mattmann C, Rimoldi D, French L E, Tschopp J (1997) Inhibition of death receptor signals by cellular FLIP. Nature 388: 190–195.

Kamens J, Paskind M, Hugunin M, Talanian R V, Allen H, Banach D, Bump N, Hackett M, Johnston C G, Li P, Mankovich J A, Terranova M, Ghayur T (1995) Identification and characterization of ICH-2, a novel member of the interleukin-1bb-converting enzyme family of cysteine proteases. J. Biol. Chem. 270: 15250–15256.

Lennon G, Auffray C, Polymeropoulos M, Soares M B (1996) The I.M.A.G.E. Consortium: An integrated molecular analysis of genomes and their expression. Genomics 33: 151–152.

Los M, Van de Craen M, Penning L C, Schenk H, Westendorp M, Baeuerle P A, Dröge W, Krammer P H, Fiers W, Schulze-Osthoff K (1995) Requirement of an ICE/CED-3 protease for Fas/APO-1-mediated apoptosis. Nature 375: 81–83.

Mertens N, Remaut E, Fiers W, (1995) Versatile, multi-featured plasmids for high-level expression of heterologous genes in *Escherichia coli*: Overproduction of human and murine cytokines. Gene 164: 9–15.

Molineaux S M, Casano F J, Rolando A M, Peterson E P, Limjuco G, Chin J, Griffin P R, Calaycay J R, Ding G J-F, Yamin T-T, Palyha O C, Luell S, Fletcher D, Miller D K, Howard A D, Thornberry N A, Kostura M J (1993) Interleukin 1bb (IL-1bb) processing in murine macrophages requires a structurally conserved homologue of human IL-1bb converting enzyme. Proc. Natl. Acad. Sci. USA 90: 1809–1813.

Muzio M, Chinnaiyan A M, Kischkel F C, O'Rourke K, Shevchenko A, Ni J, Scaffidi C, Bretz J D, Zhang M, Gentz R, Mann M, Krammer P H, Peter M E, Dixit V M (1996) FLICE, a novel FADD homologous ICE/CED-3-like protease, is recruited to the CD95 (Fas/Apo-1) death-inducing signaling complex. Cell 85: 817–827.

Nagata S (1997) Apoptosis by death factor. Cell 88: 355–365.

Nicholson D W, Ali A, Thornberry N A, Vaillancourt J P, Ding C K, Gallant M, Gareau Y, Griffin P R, Labelle M, Lazebnik Y A, Munday N A, Raju S M, Smulson M E, Yamin T-T, Yu V L, Miller D K (1995) Identification and inhibition of the ICE/CED-3 protease necessary for mammalian apoptosis. Nature 376: 37–43.

Niwa H, Yamamura K, Miyazaki J (1991) Efficient selection for high-expression transfectants with a novel eukaryotic vector. Gene 108: 193–200.

O'Mahoney J V, Adams T E (1994) Optimization of experimental variables influencing reporter gene expression in hepatoma cells following calcium phosphate transfection. DNA Cell Biol. 13: 1227–1232.

Ramage P, Cheneval D, Chvei M, Graff P, Hemmig R, Heng R, Kocher H P, Mackenzie A, Memmert K, Revesz L, Wishart W (1995) Expression, refolding, and autocatalytic proteolytic processing of the interleukin-1bb-converting enzyme precursor. J. Biol. Chem. 270: 9378–9383.

Srinivasula S M, Ahmad M, Fernandes-Alnemri T, Litwack G, Alnemri E S (1996) Molecular ordering of the Fas-apoptotic pathway: The Fas/APO-1 protease Mch5 is a CrmA-inhibitable protease that activates multiple Ced-3/ICE-like cysteine proteases. Proc. Natl. Acad. Sci. USA 93: 14486–14491.

Thompson J D, Higgins D G, Gibson T J (1994) CLUSTAL, W: Improving the sensitivity of progressive multiple sequence alignment through sequence weighting, position-specific gap penalties and weight matrix choice. Nucleic Acids Res. 22: 4673–4680.

Van Criekinge W, Beyaert R, Van de Craen M, Vandenabeele P, Schotte P, De Valck D, Fiers W (1996) Functional characterization of the prodomain of interleukin-1bb-converting enzyme. J. Biol. Chem. 271: 27245–27248.

Van de Craen M, Vandenabeele P, Declercq W, Van den brande I, Van Loo G, Molemans F, Schotte P, Van Criekinge W, Beyaert R, Fiers W (1997a) Characterization of seven murine caspase family members. FEBS Lett. 403: 61–69.

Van de Craen M, Van den brande I, Declercq W, Irmler M, Beyaert R, Tschopp J, Fiers W, Vandenabeele P (1997b) Cleavage of caspase family members by granzyme B: A comparative study in vitro. Eur. J. Immunol. 27: 1296–1299.

Villa P, Kaufmann S H, Earnshaw W C (1997) Caspases and caspase inhibitors. Trends Biochem. Sci. 22: 388–393.

Vincenz C, and Dixit V M (1997) Fas-associated death domain protein interleukin-1bb-converting enzyme 2 (FLICE2), an ICE/Ced-3 homologue, is proximally involved in CD95- and p55-mediated death signaling. J. Biol. Chem. 272: 6578–6583.

Walker N P C, Talanian R V, Brady K D, Dang L C, Bump N J, Ferenz C R, Franklin S, Ghayur T, Hackett M C, Hammill L D, Herzog L, Hugunin M, Houy W, Mankovich J A, McGuiness L, Orlewicz E, Paskind M, Pratt C A, Reis P, Summani A, Terranova M, Welch J P, Xiong L, Möller A, Tracey D E, Kamen R, Wong W W (1994) Crystal structure of the cysteine protease interleukin-1bb-converting enzyme: A $(p20/p10)_2$ homodimer. Cell 78: 343–352.

Wilson K P, Black J A, Thomson J A, Kim E E, Griffith J P, Navia M A, Murcko M A, Chambers S P, Aldape R A, Raybuck S A, Livingston D J (1994) Structure and mechanism of interleukin-1bb converting enzyme. Nature 370: 270–275.

Yang X, Chang H Y, Baltimore D (1998) Autoproteolytic activation of pro-caspases by oligomerization. Mol. Cell. 1: 319–325.

What is claimed is:

1. An isolated caspase comprising an amino acid sequence of SEQ ID NO:4.

2. A composition comprising the caspase of claim 1.

* * * * *

UNITED STATES PATENT AND TRADEMARK OFFICE
CERTIFICATE OF CORRECTION

PATENT NO. : 6,759,227 B2 Page 1 of 1
APPLICATION NO. : 09/764803
DATED : July 6, 2004
INVENTOR(S) : Marc van de Craen et al.

It is certified that error appears in the above-identified patent and that said Letters Patent is hereby corrected as shown below:

In the specification:

| | | |
|---|---|---|
| COLUMN 2, | LINE 25, | change "NC). 1" to --NO. 1-- |
| COLUMN 2, | LINE 37, | change "skin diseases The" to --skin diseases. The-- |
| COLUMN 7, | LINE 45, | delete "K" at the end of the line |
| COLUMN 7, | LINE 46, | change "öhler" to --Köhler-- |
| COLUMN 8, | LINE 29, | before ""coding sequence"" to --A "coding sequence"-- |
| COLUMN 14, | LINE 37, | change "MC 1061" to --MC1061-- |
| COLUMN 16, | LINE 9, | change "1% NP40," to --1% NP-40,-- |
| COLUMN 18, | LINE 26, | change "Bums K," to --Burns K,-- |

Signed and Sealed this

First Day of May, 2007

JON W. DUDAS
*Director of the United States Patent and Trademark Office*

SEQUENCE LISTING

<160> NUMBER OF SEQ ID NOS: 26

<210> SEQ ID NO 1
<211> LENGTH: 2213
<212> TYPE: DNA
<213> ORGANISM: Mus musculus

<400> SEQUENCE: 1

```
agacaagcca gggcctgatc ccaaggagaa ggagcacctg cttctacagc cgggcaaaac      60
aaaggtgctg aaagccagac atggagtcag agatgagtga tcctcagcca ttgcaggagg     120
aaagatatga tatgtcaggt gcccgcctgg ccctgacgct gtgtgtcacc aaagcccggg     180
agggttccga ggtagacatg gaggccctgg aacgcatgtt ccgttacctg aaatttgaaa     240
gcaccatgaa gagggatccc accgcccagc aatttctgga agagttggat gaatttcagc     300
agaccataga taattgggaa gagcctgtca gctgtgcctt tgtggtactc atggcacatg     360
gtgaggaagg cctcctcaag ggagaagatg agaagatggt cagactagaa gaccttttgg     420
aagtcttgaa caacaagaac tgcaaggccc tgagaggcaa gccaaaggtg tacatcatcc     480
aggcttgtag aggagagcac agagaccccg gtgaggaact acgtggaaat gaggaactag     540
gtggagatga ggaactaggt ggagatgagg ttgctgtgct caagaacaac ccccaaagta     600
tcccaaccta tacggatacc ctccacatct actccacggt agagggtac ctctcctata      660 gacatgacga gaaaggctct ggcttcatcc agaccctgac ggatgtgttc attcataaaa     720
aaggatccat cttagaactg acagaagaga tcacccgact tatggcaaac acggaggtga     780
tgcaggaagg aaaaccaagg aaagtgaacc ctgaagtcca aagcaccctc cggaagaagc     840
```

```
tctatttgca ataaaagaga gggcagggat ggccttcctg caggtgcttt ctctgttgac    900
accagtcttc aaagatggtt actggattct tcgttcatca cagcccttttg tccgtgtcag   960 tttcagggca agccagccag ctagagcaca ttaacaccac cttcctttcg ctggacaccc   1020
taactctgtt aatgcagcct tacattgtct tcctatagct aactgtttgc tcttttgcct   1080
caccacgcct tactctccct cctatgactc aaccgaaaat agtcatttct aattcagagg   1140
tagtagcttt ctgaaccatt tctagaaact tccaataacc tccagctaag atcgccactg   1200 tgggttttt ttcatccttg cttacaatt cgtcattgtg aagaagtcaa gggcagggaa     1260
gtacaaccat gagtgacatc acagaataaa tattcttctt caaaatcaaa gaactggagc   1320
atgaaacagt cacaccaaaa aacccaaagg acttgagcag cccttcccct ccagctacta   1380
gccttatccc aaagggtgcg tcccaaggaa gaagatgcca tgcctccagc tactagcctt   1440
atcccaaagg gcatgtccca aggaagaaga cgccatgtta gtggtcctga catctctggt   1500
gatctcagca gcatcttcag accaagcatg accaacacac acgcactctt agtcgaaata   1560
tctatgtata cttttaattg tccctgatag actctttatt cctctccaaa acccatgag    1620 ctaggcctca actaccacaa acagcctat gagctctgtt tccaggattc aataactttt    1680
tcagcccact atactcaaag cttttgaatt cccctcacaa aaacatgtcc aaatcataaa    1740
agtcacatgg ccaaatctat cacagcagtg accccacttc cttggtatcc atttctatga   1800 agaggtatc tctggaaacc tagaggagac acaaagagca ctattattta aagaccaaag    1860 gtaaaccta catctgtgtt tttcatattg gtatgactcc atccaatcag ccctcagata    1920
aattcatctc cttttctgtg aattcattct cccagaaatg ttagcatcct ctccccatgc   1980
ctctgtgccc ttgcccaatt gaccagttct ctaagcttag gtgtcccaca tggctgcccc   2040
cttctctctc ttccctttt ccactgcctc cccctcaccc ctgactccac tcctaatatt    2100
cttttttgct tgtgcggctg cctcttgcac aatgaaatgc tataattact ttcgattggt   2160
gtaatgagaa ttcagtaaac atctgtcaaa ctttgcaaaa aaaaaaaaa aaa           2213
```

<210> SEQ ID NO 2
<211> LENGTH: 257
<212> TYPE: PRT
<213> ORGANISM: Mus musculus

<400> SEQUENCE: 2

```
Met Glu Ser Glu Met Ser Asp Pro Gln Pro Leu Gln Glu Glu Arg Tyr
1               5                   10                  15

Asp Met Ser Gly Ala Arg Leu Ala Leu Thr Leu Cys Val Thr Lys Ala
            20                  25                  30

Arg Glu Gly Ser Glu Val Asp Met Glu Ala Leu Glu Arg Met Phe Arg
        35                  40                  45

Tyr Leu Lys Phe Glu Ser Thr Met Lys Arg Asp Pro Thr Ala Gln Gln
    50                  55                  60

Phe Leu Glu Glu Leu Asp Glu Phe Gln Gln Thr Ile Asp Asn Trp Glu
65                  70                  75                  80

Glu Pro Val Ser Cys Ala Phe Val Leu Met Ala His Gly Glu Glu
                85                  90                  95

Gly Leu Leu Lys Gly Glu Asp Glu Lys Met Val Arg Leu Glu Asp Leu
            100                 105                 110

Phe Glu Val Leu Asn Asn Lys Asn Cys Lys Ala Leu Arg Gly Lys Pro
        115                 120                 125
```

-continued

```
Lys Val Tyr Ile Ile Gln Ala Cys Arg Gly Glu His Arg Asp Pro Gly
            130                 135                 140
Glu Glu Leu Arg Gly Asn Glu Glu Leu Gly Gly Asp Glu Glu Leu Gly
145                 150                 155                 160
Gly Asp Glu Val Ala Val Leu Lys Asn Asn Pro Gln Ser Ile Pro Thr
                165                 170                 175
Tyr Thr Asp Thr Leu His Ile Tyr Ser Thr Val Glu Gly Tyr Leu Ser
            180                 185                 190
Tyr Arg His Asp Glu Lys Gly Ser Gly Phe Ile Gln Thr Leu Thr Asp
        195                 200                 205
Val Phe Ile His Lys Lys Gly Ser Ile Leu Glu Leu Thr Glu Glu Ile
    210                 215                 220
Thr Arg Leu Met Ala Asn Thr Glu Val Met Gln Glu Gly Lys Pro Arg
225                 230                 235                 240
Lys Val Asn Pro Glu Val Gln Ser Thr Leu Arg Lys Lys Leu Tyr Leu
                245                 250                 255
Gln
```

<210> SEQ ID NO 3
<211> LENGTH: 690
<212> TYPE: DNA
<213> ORGANISM: Homo sapiens

<400> SEQUENCE: 3

```
atgtcaggtg cccgcctggc cctaatactg tgtgtcacca agcccggga aggttccgaa      60
gaagacctgg atgctctgga acacatgttt cggcagctga gattcgaaag caccatgaaa     120
agagacccca ctgccgagca attccaggaa gagctggaaa aattccagca ggccatcgat     180
tcccgggaag atcccgtcag ttgtgccttc gtggtactca tggctcacgg agggaaggc      240
ttcctcaagg gagaagatgg ggagatggtc aagctggaga tctcttcga ggccctgaac      300
aacaagaact gccaggccct gcgagctaag cccaaggtgt acatcataca ggcctgtcga     360
ggagaacaaa gggaccccgg tgaaacagta ggtggagatg agattgtgat ggtcatcaaa     420
gacagcccac aaaccatccc aacatacaca gatgccttgc acgtttattc cacggtagag     480
ggatacatcg cctaccgaca tgatcagaaa ggctcatgct ttatccagac cctggtggat     540
gtgttcacga agaggaaagg acatatcttg gaacttctga cagaggtgac ccggcggatg     600
gcagaagcag agctggttca agaaggaaaa gcaaggaaaa cgaaccctga atccaaagc      660
accctccgga aacggctgta tctgcagtag                                      690
```

<210> SEQ ID NO 4
<211> LENGTH: 229
<212> TYPE: PRT
<213> ORGANISM: Homo sapiens

<400> SEQUENCE: 4

```
Met Ser Gly Ala Arg Leu Ala Leu Ile Leu Cys Val Thr Lys Ala Arg
1               5                   10                  15
Glu Gly Ser Glu Glu Asp Leu Asp Ala Leu Glu His Met Phe Arg Gln
            20                  25                  30
Leu Arg Phe Glu Ser Thr Met Lys Arg Asp Pro Thr Ala Glu Gln Phe
        35                  40                  45
Gln Glu Glu Leu Glu Lys Phe Gln Gln Ala Ile Asp Ser Arg Glu Asp
    50                  55                  60
Pro Val Ser Cys Ala Phe Val Val Leu Met Ala His Gly Arg Glu Gly
```

-continued

```
                65                   70                   75                   80
            Phe Leu Lys Gly Glu Asp Gly Glu Met Val Lys Leu Glu Asn Leu Phe
                            85                   90                   95

Glu Ala Leu Asn Asn Lys Asn Cys Gln Ala Leu Arg Ala Lys Pro Lys
                        100                 105                 110

Val Tyr Ile Ile Gln Ala Cys Arg Gly Glu Gln Arg Asp Pro Gly Glu
                    115                 120                 125

Thr Val Gly Gly Asp Glu Ile Val Met Val Ile Lys Asp Ser Pro Gln
                130                 135                 140

Thr Ile Pro Thr Tyr Thr Asp Ala Leu His Val Tyr Ser Thr Val Glu
            145                 150                 155                 160

Gly Tyr Ile Ala Tyr Arg His Asp Gln Lys Gly Ser Cys Phe Ile Gln
                            165                 170                 175

Thr Leu Val Asp Val Phe Thr Lys Arg Lys Gly His Ile Leu Glu Leu
                        180                 185                 190

Leu Thr Glu Val Thr Arg Arg Met Ala Glu Ala Glu Leu Val Gln Glu
                    195                 200                 205

Gly Lys Ala Arg Lys Thr Asn Pro Glu Ile Gln Ser Thr Leu Arg Lys
                210                 215                 220

Arg Leu Tyr Leu Gln
            225

<210> SEQ ID NO 5
<211> LENGTH: 38
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<223> OTHER INFORMATION: Description of Artificial Sequence: PCR primer

<400> SEQUENCE: 5
gcgaagcttc caccatggag tcagagatga gtgatcct                              38

<210> SEQ ID NO 6
<211> LENGTH: 35
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<223> OTHER INFORMATION: Description of Artificial Sequence: PCR primer

<400> SEQUENCE: 6
gggagaagcg gccgcttgca aatagagctt cttcc                                35

<210> SEQ ID NO 7
<211> LENGTH: 37
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Description of Artificial Sequence: primer

<400> SEQUENCE: 7
gcggatatcc accatggagt cagagatgag tgatcct                              37

<210> SEQ ID NO 8
```

```
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Description of Artificial Sequence: primer

<400> SEQUENCE: 8
gcggatatct tattgcaaat agagcttctt cc                                    32

<210> SEQ ID NO 9
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Description of Artificial Sequence: primer

<400> SEQUENCE: 9
gcggatatct gaggttgctg tgctcaagaa caacc                                 35

<210> SEQ ID NO 10
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Description of Artificial Sequence: primer

<400> SEQUENCE: 10
gcggaattcg atatcttatt gcaaatagag cttcttcc                              38

<210> SEQ ID NO 11
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Description of Artificial Sequence: primer

<400> SEQUENCE: 11
gctcaccatg gatgatgata tcgcc                                            25

<210> SEQ ID NO 12
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Description of Artificial Sequence: primer

<400> SEQUENCE: 12
ggatgcctct cttgctctgg gcctc                                            25

<210> SEQ ID NO 13
<211> LENGTH: 34
<212> TYPE: DNA
<213> ORGANISM: Artificial
<220> FEATURE:
```

```
<221> NAME/KEY: misc_feature
<223> OTHER INFORMATION: Description of Artificial Sequence: primer F1

<400> SEQUENCE: 13
gcggatatcc atggagtcag agatgagtga tcct                                34

<210> SEQ ID NO 14
<211> LENGTH: 34
<212> TYPE: DNA
<213> ORGANISM: Artificial Sequence
<220> FEATURE:
<223> OTHER INFORMATION: Primer F2
<220> FEATURE:
<221> NAME/KEY: misc_feature
<223> OTHER INFORMATION: Description of Artificial Sequence: primer F2

<400> SEQUENCE: 14
gcggatatca cctcagccat tgcaggagga aaga                                34

<210> SEQ ID NO 15
<211> LENGTH: 37
<212> TYPE: DNA
<213> ORGANISM: Artificial Sequence
<220> FEATURE:
<223> OTHER INFORMATION: Primer F3
<220> FEATURE:
<221> NAME/KEY: misc_feature
<223> OTHER INFORMATION: Description of Artificial Sequence: primer F3

<400> SEQUENCE: 15
gcggatatcc atgtcaggtg cccgcctggc cctgacg                             37

<210> SEQ ID NO 16
<211> LENGTH: 38
<212> TYPE: DNA
<213> ORGANISM: Artificial Sequence
<220> FEATURE:
<223> OTHER INFORMATION: Primer R
<220> FEATURE:
<221> NAME/KEY: misc_feature
<223> OTHER INFORMATION: Description of Artificial Sequence: primer R

<400> SEQUENCE: 16
gcggaattcg atatcttatt gcaaatagag cttcttcc                            38

<210> SEQ ID NO 17
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Description of Artificial Sequence: primer

<400> SEQUENCE: 17
gcggatatcc agtgagtcac ggacttcaga caaag                               35

<210> SEQ ID NO 18
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Description of Artificial Sequence: primer

<400> SEQUENCE: 18
```

```
gcggatatcg aattctcatt agggagggaa gaagagcttc                              40
```

<210> SEQ ID NO 19
<211> LENGTH: 43
<212> TYPE: DNA
<213> ORGANISM: Artificial Sequence
<220> FEATURE:
<223> OTHER INFORMATION: Primer YF
<220> FEATURE:
<221> NAME/KEY: misc_feature
<223> OTHER INFORMATION: Description of Artificial Sequence: primer YF

<400> SEQUENCE: 19

```
aaagagatcg aattcgccat ggagtcagag atgagtgatc ctc                         43
```

<210> SEQ ID NO 20
<211> LENGTH: 48
<212> TYPE: DNA
<213> ORGANISM: Artificial Sequence
<220> FEATURE:
<223> OTHER INFORMATION: Primer YR
<220> FEATURE:
<221> NAME/KEY: misc_feature
<223> OTHER INFORMATION: Description of Artificial Sequence: primer YR

<400> SEQUENCE: 20

```
atagatctct gcaggtcgac gttattgcaa atagagcttc ttccggag                    48
```

<210> SEQ ID NO 21
<211> LENGTH: 29
<212> TYPE: DNA
<213> ORGANISM: Artificial Sequence
<220> FEATURE:
<223> OTHER INFORMATION: Primer YCSF
<220> FEATURE:
<221> NAME/KEY: misc_feature
<223> OTHER INFORMATION: Description of Artificial Sequence: primer YCSF

<400> SEQUENCE: 21

```
catccaggct agtagaggag agcacagag                                         29
```

<210> SEQ ID NO 22
<211> LENGTH: 29
<212> TYPE: DNA
<213> ORGANISM: Artificial Sequence
<220> FEATURE:
<223> OTHER INFORMATION: Primer YCSR
<220> FEATURE:
<221> NAME/KEY: misc_feature
<223> OTHER INFORMATION: Description of Artificial Sequence: primer YCSR

<400> SEQUENCE: 22

```
ctctgtgctc tcctctacta gcctggatg                                         29
```

<210> SEQ ID NO 23
<211> LENGTH: 383
<212> TYPE: PRT
<213> ORGANISM: Homo sapiens
<220> FEATURE:
<221> NAME/KEY: SITE
<222> LOCATION: (1)..(383)
<223> OTHER INFORMATION: human capase-1 (genbank)

<400> SEQUENCE: 23

```
Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
```

```
                 20                  25                  30
Arg Val Leu Asn Lys Glu Glu Met Glu Lys Val Lys Arg Glu Asn Ala
             35                  40                  45

Thr Val Met Asp Lys Thr Arg Ala Leu Ile Asp Ser Val Ile Pro Lys
 50                  55                  60

Gly Ala Gln Ala Cys Gln Ile Cys Ile Thr Tyr Ile Cys Glu Glu Asp
 65                  70                  75                  80

Ser Tyr Leu Ala Gly Thr Leu Gly Leu Ser Ala Ala Pro Gln Ala Val
                 85                  90                  95

Gln Asp Asn Pro Ala Met Pro Thr Ser Ser Gly Ser Glu Gly Asn Val
             100                 105                 110

Lys Leu Cys Ser Leu Glu Glu Ala Gln Arg Ile Trp Lys Gln Lys Ser
             115                 120                 125

Ala Glu Ile Tyr Pro Ile Met Asp Lys Ser Ser Arg Thr Arg Leu Ala
             130                 135                 140

Leu Ile Ile Cys Asn Glu Glu Phe Asp Ser Ile Pro Arg Arg Thr Gly
145                 150                 155                 160

Ala Glu Val Asp Ile Thr Gly Met Thr Met Leu Leu Gln Asn Leu Gly
                 165                 170                 175

Tyr Ser Val Asp Val Lys Lys Asn Leu Thr Ala Ser Asp Met Thr Thr
             180                 185                 190

Glu Leu Glu Ala Phe Ala His Arg Pro Glu His Lys Thr Ser Asp Ser
             195                 200                 205

Thr Phe Leu Val Phe Met Ser His Gly Ile Arg Glu Gly Ile Cys Gly
             210                 215                 220

Lys Lys His Ser Glu Gln Val Pro Asp Ile Leu Gln Leu Asn Ala Ile
225                 230                 235                 240

Phe Asn Met Leu Asn Thr Lys Asn Cys Pro Ser Leu Lys Asp Lys Pro
                 245                 250                 255

Lys Val Ile Ile Ile Gln Ala Cys Arg Gly Asp Ser Pro Gly Val Val
             260                 265                 270

Trp Phe Lys Asp Ser Val Gly Val Ser Gly Asn Leu Ser Leu Pro Thr
             275                 280                 285

Thr Glu Glu Phe Glu Asp Asp Ala Ile Lys Lys Ala His Ile Glu Lys
             290                 295                 300

Asp Phe Ile Ala Phe Cys Ser Ser Thr Pro Asp Asn Val Ser Trp Arg
305                 310                 315                 320

His Pro Thr Met Gly Ser Val Phe Ile Gly Arg Leu Ile Glu His Met
                 325                 330                 335

Gln Glu Tyr Ala Cys Ser Cys Asp Val Glu Glu Ile Phe Arg Lys Val
             340                 345                 350

Arg Phe Ser Phe Glu Gln Pro Asp Gly Arg Ala Gln Met Pro Thr Thr
             355                 360                 365

Glu Arg Val Thr Leu Thr Arg Cys Phe Tyr Leu Phe Pro Gly His
             370                 375                 380

<210> SEQ ID NO 24
<211> LENGTH: 242
<212> TYPE: PRT
<213> ORGANISM: Artificial Sequence
<220> FEATURE:
<223> OTHER INFORMATION: Predicted (genscan program) human caspase-1
<220> FEATURE:
<221> NAME/KEY: misc_feature
<223> OTHER INFORMATION: Description of Artificial Sequence: predicted
      (genscan program) human caspase-14
```

-continued

```
<400> SEQUENCE: 24

Met Asp Asn Phe Arg Glu Asn Ile Thr Glu Lys Tyr Asp Met Ser Gly
1               5                   10                  15

Ala Arg Leu Ala Leu Ile Leu Cys Val Thr Lys Ala Arg Glu Gly Ser
            20                  25                  30

Glu Glu Asp Leu Asp Ala Leu Glu His Met Phe Arg Gln Leu Arg Phe
        35                  40                  45

Glu Ser Thr Met Lys Arg Asp Pro Thr Ala Glu Gln Phe Gln Glu Glu
    50                  55                  60

Leu Glu Lys Phe Gln Gln Ala Ile Asp Ser Arg Glu Asp Pro Val Ser
65                  70                  75                  80

Cys Ala Phe Val Val Leu Met Ala His Gly Arg Glu Gly Phe Leu Lys
                85                  90                  95

Gly Glu Asp Gly Glu Met Val Lys Leu Glu Asn Leu Phe Glu Ala Leu
            100                 105                 110

Asn Asn Lys Asn Cys Gln Ala Leu Arg Ala Lys Pro Lys Val Tyr Ile
        115                 120                 125

Ile Gln Ala Cys Arg Gly Glu Gln Arg Asp Pro Gly Glu Thr Val Gly
    130                 135                 140

Gly Asp Glu Ile Val Met Val Ile Lys Asp Ser Pro Gln Thr Ile Pro
145                 150                 155                 160

Thr Tyr Thr Asp Ala Leu His Val Tyr Ser Thr Val Glu Gly Tyr Ile
                165                 170                 175

Ala Tyr Arg His Asp Gln Lys Gly Ser Cys Phe Ile Gln Thr Leu Val
            180                 185                 190

Asp Val Phe Thr Lys Arg Lys Gly His Ile Leu Glu Leu Leu Thr Glu
        195                 200                 205

Val Thr Arg Arg Met Ala Glu Ala Glu Leu Val Gln Glu Gly Lys Ala
    210                 215                 220

Arg Lys Thr Asn Pro Glu Ile Gln Ser Thr Leu Arg Lys Arg Leu Tyr
225                 230                 235                 240

Leu Gln

<210> SEQ ID NO 25
<211> LENGTH: 242
<212> TYPE: PRT
<213> ORGANISM: Homo sapiens

<400> SEQUENCE: 25

Met Ser Asn Pro Arg Ser Leu Glu Glu Glu Lys Tyr Asp Met Ser Gly
1               5                   10                  15

Ala Arg Leu Ala Leu Ile Leu Cys Val Thr Lys Ala Arg Glu Gly Ser
            20                  25                  30

Glu Glu Asp Leu Asp Ala Leu Glu His Met Phe Arg Gln Leu Arg Phe
        35                  40                  45

Glu Ser Thr Met Lys Arg Asp Pro Thr Ala Glu Gln Phe Gln Glu Glu
    50                  55                  60

Leu Glu Lys Phe Gln Gln Ala Ile Asp Ser Arg Glu Asp Pro Val Ser
65                  70                  75                  80

Cys Ala Phe Val Val Leu Met Ala His Gly Arg Glu Gly Phe Leu Lys
                85                  90                  95

Gly Glu Asp Gly Glu Met Val Lys Leu Glu Asn Leu Phe Glu Ala Leu
            100                 105                 110
```

```
Asn Asn Lys Asn Cys Gln Ala Leu Arg Ala Lys Pro Lys Val Tyr Ile
            115                 120                 125
Ile Gln Ala Cys Arg Gly Glu Gln Arg Asp Pro Gly Glu Thr Val Gly
        130                 135                 140
Gly Asp Glu Ile Val Met Val Ile Lys Asp Ser Pro Gln Thr Ile Pro
145                 150                 155                 160
Thr Tyr Thr Asp Ala Leu His Val Tyr Ser Thr Val Glu Gly Tyr Ile
                165                 170                 175
Ala Tyr Arg His Asp Gln Lys Gly Ser Cys Phe Ile Gln Thr Leu Val
            180                 185                 190
Asp Val Phe Thr Lys Arg Lys Gly His Ile Leu Glu Leu Leu Thr Glu
        195                 200                 205
Val Thr Arg Arg Met Ala Glu Ala Glu Leu Val Gln Glu Gly Lys Ala
    210                 215                 220
Arg Lys Thr Asn Pro Glu Ile Gln Ser Thr Leu Arg Lys Arg Leu Tyr
225                 230                 235                 240
Leu Gln

<210> SEQ ID NO 26
<211> LENGTH: 242
<212> TYPE: PRT
<213> ORGANISM: Homo sapiens

<400> SEQUENCE: 26

Met Asp Glu Phe Arg Glu Asn Ile Thr Glu Lys Tyr Asp Met Ser Gly
1               5                   10                  15
Ala Arg Leu Ala Leu Ile Leu Cys Val Thr Lys Ala Arg Glu Gly Ser
            20                  25                  30
Glu Glu Asp Leu Asp Ala Leu Glu His Met Phe Arg Gln Leu Arg Phe
        35                  40                  45
Glu Ser Thr Met Lys Arg Asp Pro Thr Ala Glu Gln Phe Gln Glu Glu
    50                  55                  60
Leu Glu Lys Phe Gln Gln Ala Ile Asp Ser Arg Glu Asp Pro Val Ser
65                  70                  75                  80
Cys Ala Phe Val Val Leu Met Ala His Gly Arg Glu Gly Phe Leu Lys
                85                  90                  95
Gly Glu Asp Gly Glu Met Val Lys Leu Glu Asn Leu Phe Glu Ala Leu
            100                 105                 110
Asn Asn Lys Asn Cys Gln Ala Leu Arg Ala Lys Pro Lys Val Tyr Ile
            115                 120                 125
Ile Gln Ala Cys Arg Gly Glu Gln Arg Asp Pro Gly Glu Thr Val Gly
        130                 135                 140
Gly Asp Glu Ile Val Met Val Ile Lys Asp Ser Pro Gln Thr Ile Pro
145                 150                 155                 160
Thr Tyr Thr Asp Ala Leu His Val Tyr Ser Thr Val Glu Gly Tyr Ile
                165                 170                 175
Ala Tyr Arg His Asp Gln Lys Gly Ser Cys Phe Ile Gln Thr Leu Val
            180                 185                 190
Asp Val Phe Thr Lys Arg Lys Gly His Ile Leu Glu Leu Leu Thr Glu
        195                 200                 205
Val Thr Arg Arg Met Ala Glu Ala Glu Leu Val Gln Glu Gly Lys Ala
    210                 215                 220
```

-continued

```
Arg Lys Thr Asn Pro Glu Ile Gln Ser Thr Leu Arg Lys Arg Leu Tyr
225                 230                 235                 240

Leu Gln
```